US011622818B2

United States Patent
Siemionow et al.

(10) Patent No.: US 11,622,818 B2
(45) Date of Patent: Apr. 11, 2023

(54) GRAPHICAL USER INTERFACE FOR DISPLAYING AUTOMATICALLY SEGMENTED INDIVIDUAL PARTS OF ANATOMY IN A SURGICAL NAVIGATION SYSTEM

(71) Applicant: HOLO SURGICAL INC., Deerfield, IL (US)

(72) Inventors: Krzysztof B. Siemionow, Chicago, IL (US); Cristian J. Luciano, Chicago, IL (US); Edwing Isaac Mejia Orozco, Warsaw (PL)

(73) Assignee: HOLO SURGICAL INC., Deerfield, IL (US)

( * ) Notice: Subject to any disclaimer, the term of this patent is extended or adjusted under 35 U.S.C. 154(b) by 3 days.

(21) Appl. No.: 16/186,549

(22) Filed: Nov. 11, 2018

(65) Prior Publication Data
US 2019/0142519 A1    May 16, 2019

(30) Foreign Application Priority Data
Nov. 11, 2017  (EP) .................................... 17201224

(51) Int. Cl.
*A61B 34/10*  (2016.01)
*A61B 5/00*  (2006.01)
(Continued)

(52) U.S. Cl.
CPC ............ *A61B 34/25* (2016.02); *A61B 5/7267* (2013.01); *A61B 34/10* (2016.02); *A61B 34/30* (2016.02);
(Continued)

(58) Field of Classification Search
CPC .... A61B 2017/00216; A61B 2034/102; A61B 2034/105; A61B 2034/107;
(Continued)

(56) References Cited

U.S. PATENT DOCUMENTS 6,405,072 B1   6/2002  Cosman
8,314,815 B2  11/2012  Navab et al.
(Continued)

FOREIGN PATENT DOCUMENTS

CN   106600568 A    4/2017
EP      2922025       9/2015
(Continued)

OTHER PUBLICATIONS

Mao et al (Image Restoration Using Very Deep Convolutional Encoder-Decoder Networks with Symmetric Skip Connections, 29th Conference on Neural Information Processing Systems (NIPS 2016), Barcelona, Spain). (Year: 2016).*
(Continued)

*Primary Examiner* — Yi-Shan Yang
*Assistant Examiner* — Alexei Bykhovski
(74) *Attorney, Agent, or Firm* — Cooley LLP

(57) ABSTRACT

A surgical navigation system includes a source of a patient anatomy data, wherein the patient anatomy data comprises a three-dimensional reconstruction of a segmented model comprising at least two sections representing parts of the anatomy. A surgical navigation image generator is configured to generate a surgical navigation image comprising the patient anatomy. A 3D display system is configured to show the surgical navigation image wherein the display of the patient anatomy is selectively configurable such that at least one section of the anatomy is displayed and at least one other section of the anatomy is not displayed.

21 Claims, 20 Drawing Sheets

(51) Int. Cl.
  *A61B 34/20* (2016.01)
  *A61B 90/00* (2016.01)
  *G06F 3/01* (2006.01)
  *G06T 19/00* (2011.01)
  *G06T 7/11* (2017.01)
  *G06T 5/00* (2006.01)
  *A61B 34/00* (2016.01)
  *G02B 27/01* (2006.01)
  *A61B 34/30* (2016.01)
  *A61B 90/50* (2016.01)
  *A61B 17/00* (2006.01)
  *G06K 9/62* (2022.01)
  *G06T 7/20* (2017.01)

(52) U.S. Cl.
  CPC .............. *A61B 90/36* (2016.02); *A61B 90/37* (2016.02); *G02B 27/017* (2013.01); *G02B 27/0172* (2013.01); *G06F 3/012* (2013.01); *G06F 3/013* (2013.01); *G06T 5/002* (2013.01); *G06T 7/11* (2017.01); *G06T 19/006* (2013.01); *A61B 34/20* (2016.02); *A61B 2017/00216* (2013.01); *A61B 2034/102* (2016.02); *A61B 2034/105* (2016.02); *A61B 2034/107* (2016.02); *A61B 2034/2055* (2016.02); *A61B 2034/2063* (2016.02); *A61B 2034/2068* (2016.02); *A61B 2090/363* (2016.02); *A61B 2090/365* (2016.02); *A61B 2090/367* (2016.02); *A61B 2090/368* (2016.02); *A61B 2090/3618* (2016.02); *A61B 2090/372* (2016.02); *A61B 2090/3762* (2016.02); *A61B 2090/3983* (2016.02); *A61B 2090/502* (2016.02); *G02B 2027/0134* (2013.01); *G02B 2027/0136* (2013.01); *G02B 2027/0138* (2013.01); *G02B 2027/0178* (2013.01); *G02B 2027/0187* (2013.01); *G02B 2027/0196* (2013.01); *G06K 9/6257* (2013.01); *G06T 7/20* (2013.01); *G06T 2207/10081* (2013.01); *G06T 2207/20081* (2013.01); *G06T 2207/20084* (2013.01); *G06T 2207/30012* (2013.01); *G06T 2207/30208* (2013.01); *G06T 2219/004* (2013.01); *G06V 2201/033* (2022.01)

(58) Field of Classification Search
  CPC .... A61B 2034/2055; A61B 2034/2063; A61B 2034/2068; A61B 2090/3618; A61B 2090/363; A61B 2090/365; A61B 2090/367; A61B 2090/368; A61B 2090/372; A61B 2090/3762; A61B 2090/3983; A61B 2090/502; A61B 34/10; A61B 34/20; A61B 34/25; A61B 34/30; A61B 5/7267; A61B 90/36; A61B 90/37; G02B 2027/0134; G02B 2027/0136; G02B 2027/0138; G02B 2027/0178; G02B 2027/0187; G02B 2027/0196; G02B 27/017; G02B 27/0172; G06F 3/012; G06F 3/013; G06K 2209/055; G06K 9/6257; G06T 19/006; G06T 2207/10081; G06T 2207/20081; G06T 2207/20084; G06T 2207/30012; G06T 2207/30208; G06T 2219/004; G06T 5/002; G06T 7/11; G06T 7/20
  See application file for complete search history.

(56) References Cited

U.S. PATENT DOCUMENTS

| | | | |
|---|---|---|---|
| 8,933,935 | B2 | 1/2015 | Yang et al. |
| 9,275,192 | B2 | 3/2016 | Kang et al. |
| 9,289,267 | B2 | 3/2016 | Sauer et al. |
| 9,510,771 | B1 | 12/2016 | Finley et al. |
| 9,532,848 | B2 | 1/2017 | Amiot et al. |
| 9,572,548 | B2 | 2/2017 | Moctezuma de la Barrera |
| 9,785,246 | B2 | 10/2017 | Isaacs et al. |
| 9,949,700 | B2 | 4/2018 | Razzaque et al. |
| 10,013,808 | B2 | 7/2018 | Jones et al. |
| 10,016,243 | B2 | 7/2018 | Esterberg |
| 10,080,623 | B2 | 9/2018 | Saito |
| 10,105,187 | B2 | 10/2018 | Corndorf et al. |
| 10,134,166 | B2 | 11/2018 | Benishti et al. |
| 10,191,615 | B2 | 1/2019 | Helm et al. |
| 10,194,131 | B2 | 1/2019 | Casas |
| 10,292,768 | B2 | 5/2019 | Lang |
| 10,405,926 | B2 | 9/2019 | Frank et al. |
| 10,624,702 | B2 | 4/2020 | Moctezuma et al. |
| 10,646,283 | B2 | 5/2020 | Johnson et al. |
| 10,646,285 | B2 | 5/2020 | Siemionow et al. |
| 10,653,497 | B2 | 5/2020 | Crawford et al. |
| 10,667,864 | B2 | 6/2020 | Feilkas et al. |
| 10,675,094 | B2 | 6/2020 | Crawford et al. |
| 10,736,699 | B2 | 8/2020 | Ronen et al. |
| 10,788,672 | B2 * | 9/2020 | Yadav ................... G06T 11/60 |
| 10,835,322 | B2 | 11/2020 | Ruckel et al. |
| 10,939,977 | B2 | 3/2021 | Messinger et al. |
| 10,951,872 | B2 | 3/2021 | Casas |
| 11,090,019 | B2 | 8/2021 | Siemionow et al. |
| 11,278,359 | B2 | 3/2022 | Siemionow et al. |
| 2002/0082498 | A1 | 6/2002 | Wendt et al. |
| 2004/0047044 | A1 | 3/2004 | Dalton |
| 2005/0190446 | A1 | 9/2005 | Kuerz et al. |
| 2005/0289472 | A1 | 12/2005 | Morita et al. |
| 2006/0176242 | A1 | 8/2006 | Jaramaz et al. |
| 2008/0144773 | A1 | 6/2008 | Bar-Zohar et al. |
| 2010/0328433 | A1 | 12/2010 | Li |
| 2011/0229005 | A1 | 9/2011 | Harder et al. |
| 2011/0311113 | A1 * | 12/2011 | Baumgart ............... G06T 11/00 382/128 |
| 2012/0314224 | A1 | 12/2012 | Luellau |
| 2013/0226190 | A1 | 8/2013 | Mckinnon et al. |
| 2015/0018622 | A1 | 1/2015 | Tesar et al. |
| 2015/0125033 | A1 | 5/2015 | Murphy et al. |
| 2015/0177598 | A1 | 6/2015 | Mima et al. |
| 2015/0201895 | A1 | 7/2015 | Suzuki |
| 2015/0264339 | A1 | 9/2015 | Riedel |
| 2016/0035139 | A1 | 2/2016 | Fuchs et al. |
| 2016/0176242 | A1 | 6/2016 | Nakamata |
| 2016/0187969 | A1 | 6/2016 | Larsen et al. |
| 2016/0191887 | A1 | 6/2016 | Casas |
| 2016/0278875 | A1 | 9/2016 | Crawford et al. |
| 2016/0324580 | A1 | 11/2016 | Esterberg |
| 2016/0328630 | A1 | 11/2016 | Han et al. |
| 2017/0024903 | A1 | 1/2017 | Razzaque |
| 2017/0042631 | A1 | 2/2017 | Doo et al. |
| 2017/0056115 | A1 | 3/2017 | Corndorf et al. |
| 2017/0084036 | A1 | 3/2017 | Pheiffer et al. |
| 2017/0105802 | A1 | 4/2017 | Taraschi et al. |
| 2017/0112575 | A1 * | 4/2017 | Li ......................... A61B 34/10 |
| 2017/0258526 | A1 * | 9/2017 | Lang ................... A61B 17/155 |
| 2017/0323062 | A1 | 11/2017 | Djajadiningrat et al. |
| 2017/0329402 | A1 | 11/2017 | Riedel |
| 2017/0360395 | A1 | 12/2017 | Razzaque |
| 2018/0012416 | A1 | 1/2018 | Jones et al. |
| 2018/0042681 | A1 | 2/2018 | Jagga |
| 2018/0078316 | A1 | 3/2018 | Schaewe et al. |
| 2018/0082480 | A1 | 3/2018 | White et al. |
| 2018/0140362 | A1 | 5/2018 | Cali et al. |
| 2018/0174311 | A1 | 6/2018 | Kluckner et al. |
| 2018/0185113 | A1 | 7/2018 | Gregorson et al. |
| 2018/0225993 | A1 | 8/2018 | Buras et al. |
| 2018/0271484 | A1 | 9/2018 | Whisler |
| 2018/0276813 | A1 | 9/2018 | Gur et al. |
| 2018/0303558 | A1 | 10/2018 | Thomas |

(56) References Cited

U.S. PATENT DOCUMENTS

| | | |
|---|---|---|
| 2018/0311012 A1 | 11/2018 | Moctezuma et al. |
| 2019/0029757 A1 | 1/2019 | Roh et al. |
| 2019/0053851 A1 | 2/2019 | Siemionow et al. |
| 2019/0105009 A1 | 4/2019 | Siemionow et al. |
| 2019/0130575 A1 | 5/2019 | Chen et al. |
| 2019/0175285 A1 | 6/2019 | Siemionow et al. |
| 2019/0192230 A1 | 6/2019 | Siemionow et al. |
| 2019/0201106 A1 | 7/2019 | Siemionow et al. |
| 2019/0307513 A1 | 10/2019 | Leung et al. |
| 2019/0333626 A1 | 10/2019 | Mansi et al. |
| 2020/0051274 A1 | 2/2020 | Siemionow et al. |
| 2020/0151507 A1 | 5/2020 | Siemionow et al. |
| 2020/0229877 A1 | 7/2020 | Siemionow et al. |
| 2020/0327721 A1 | 10/2020 | Siemionow et al. |
| 2020/0410687 A1 | 12/2020 | Siemionow et al. |
| 2021/0267698 A1 | 9/2021 | Siemionow et al. |

FOREIGN PATENT DOCUMENTS

| | | |
|---|---|---|
| EP | 3 151 736 A2 | 4/2017 |
| EP | 3 221 809 A1 | 9/2017 |
| EP | 3 361 979 A1 | 8/2018 |
| EP | 3 432 263 A1 | 1/2019 |
| GB | 2536650 | 9/2016 |
| WO | WO 2007/110820 A2 | 10/2007 |
| WO | WO 2007/115826 A2 | 10/2007 |
| WO | 2012018560 | 2/2012 |
| WO | WO 2012/027574 A1 | 3/2012 |
| WO | WO 2014/036473 A1 | 3/2014 |
| WO | WO 2015/058816 A1 | 4/2015 |
| WO | WO 2016/010719 A1 | 1/2016 |
| WO | WO 2016/010737 A2 | 1/2016 |
| WO | WO 2016/078919 A1 | 5/2016 |
| WO | WO 2017/003453 A1 | 1/2017 |
| WO | WO 2017/066373 A1 | 4/2017 |
| WO | WO 2017/083494 A1 | 5/2017 |
| WO | 2017091833 | 6/2017 |
| WO | WO 2018/048575 A1 | 3/2018 |
| WO | WO 2018/052966 A1 | 3/2018 |
| WO | WO 2018/057564 A1 | 3/2018 |
| WO | WO 2018/063528 A1 | 4/2018 |
| WO | WO 2018/067794 A1 | 4/2018 |
| WO | WO 2018/140415 A1 | 8/2018 |
| WO | WO 2018/171880 A1 | 9/2018 |
| WO | WO 2018/206086 A1 | 11/2018 |
| WO | WO 2019/005722 A1 | 1/2019 |
| WO | WO 2019/023625 A1 | 1/2019 |
| WO | WO 2019/118215 A1 | 6/2019 |
| WO | WO 2019/195926 A1 | 10/2019 |
| WO | WO 2020/109903 A1 | 6/2020 |
| WO | WO 2020/121126 A1 | 6/2020 |
| WO | WO 2020/123928 A1 | 6/2020 |
| WO | WO 2020/231880 A1 | 11/2020 |

OTHER PUBLICATIONS

C. Cernazanu-Glavan et al. "Segmentation of Bone Structure in X-Ray Images Using Convolutional Neutral Network" 10th International Conference on Development and Applications Systems, vol. 13, No. 1. Jan. 1, 2013 DOI:10.4316/AECE.2013.01015.

Hu Chen et al "Alow-Dose CT via Convolutional Neural Network" Biomedical Optics Express, vol. 8, No. 2. Jan. 9, 2017 DOI:10.1364/BOE.8.000679.

U.S. Appl. No. 16/101,459, filed Aug. 12, 2018.
U.S. Appl. No. 16/154,747, filed Oct. 9, 2018.
U.S. Appl. No. 16/217,073, filed Dec. 12, 2018.
U.S. Appl. No. 17/145,178, filed Jan. 8, 2021.
U.S. Appl. No. 16/217,061, filed Dec. 12, 2018.
U.S. Appl. No. 16/236,663, filed Dec. 31, 2018.
U.S. Appl. No. 16/537,645, filed Aug. 12, 2019.
U.S. Appl. No. 16/677,707, filed Nov. 8, 2019.
U.S. Appl. No. 16/833,750, filed Mar. 30, 2020.
U.S. Appl. No. 16/897,315, filed Jun. 10, 2020.
Non-Final Office Action dated Nov. 16, 2020 for U.S. Appl. No. 16/101,459, 43 pages.
Non-Final Office Action dated Sep. 16, 2019 for U.S. Appl. No. 16/059,061, 20 pages.
Non-Final Office Action dated Jul. 10, 2020 for U.S. Appl. No. 16/842,793, 23 pages.
Non-Final Office Action dated Oct. 27, 2020 for U.S. Appl. No. 16/537,645, 18 pages.
Extended European Search Report dated Oct. 25, 2017 for European Application No. 17186306.1, 14 pages.
Extended European Search Report dated Oct. 27, 2017 for European Application No. 17186307.9, 15 pages.
Extended European Search Report dated Feb. 16, 2018 for European Application No. 17195826.7, 8 pages.
Extended European Search Report dated Feb. 12, 2018 for European Application No. 17201224.7, 14 pages.
Extended European Search Report dated Feb. 27, 2018 for European Application No. 17206558.3, 13 pages.
Communication Pursuant to Article 94(3) dated Mar. 18, 2020 for European Application No. 17206558.3, 11 pages.
Extended European Search Report dated Apr. 17, 2019 for European Application No. 18211806.7, 8 pages.
Communication Pursuant to Article 94(3) dated Apr. 22, 2020 for European Application No. 18211806.7, 6 pages.
Extended European Search Report dated Jul. 5, 2018 for European Application No. 18150376.4, 10 pages.
Extended European Search Report dated Feb. 26, 2019 for European Application No. 18188557.5, 9 pages.
Extended European Search Report dated Feb. 1, 2019 for European Application No. 18205207.6, 9 pages.
Extended European Search Report dated Nov. 4, 2019 for European Application No. 19169136.9, 5 pages.
Extended European Search Report dated Oct. 23, 2019 for European Application No. 19179411.4, 8 pages.
Christ, P. F. et al., "Automatic Liver and Lesion Segmentation in CT Using Cascaded Fully Convolutional Neural Networks and 3D Conditional Random Fields," Oct. 7, 2016, 8 pages; arXiv:1610.02177v1.
Cramer, J., "Medical Image Segmentation and Design Tutorial with MevisLab," Apr. 27, 2016, retrieved on Jan. 26, 2018 from https://www.youtube.com/watch?v=PHf3Np37zTW, 1 page.
Egmont-Petersen, M. & Arts, T., "Recognition of radiopaque markers in X-ray images using a neural network as nonlinear filter," Pattern Recognition Letters, 20:521-533 (1999).
Fitzpatrick, J. M., "The role of registration in accurate surgical guidance," Proceedings of the Institute of Mechanical Engineering Medicine, Part H: Journal of Engineering in Medicine, 224(5):607-622 (2010); doi:10.1243/09544119JEIM589.
Gros, C. et al., "Automatic segmentation of the spinal cord and intramedullary multiple sclerosis lesions with convolutional neural networks," Neuroimage, 184:901-915 (2019).
Han, Z. et al., "Spine-GAN: Semantic segmentation of multiple spinal structures," Med Image Anal., 50:23-35 (2018); doi:10.1016/j.media.2018.08.005. Epub Aug. 25, 2018.
Jiménez-Pastor, A. et al., "Automatic localization and identification of vertebrae in spine CT scans by combining Deep Learning with morphological image processing techniques," European Congress of Radiology (ECR) 2018, Mar. 4, 2018, retrieved from the Internet at: https://quibim.com/wp-content/uploads/2018/03/3_ECR2018_AJP, 30 pages.
Krinninger, M., "Ein System zur Endoskopführung in der HNO-Chirurgie," Dissertation, Mar. 15, 2011, XP055450605, Technischen Universitat München, 151 pages.
Krinninger, M., "Ein System zur Endoskopführung in der HNO-Chirurgie," Dissertation, Mar. 15, 2011, XP055450605, Technischen Universität München; retrieved on Feb. 13, 2018 from https://mediatum.ub.tum.de/doc/998215/998215.pdf.—English Abstract, 1 page.
Krishnan, R. et al., "Automated Fiducial Marker Detection for Patient Registration in Image-Guided Neurosurgery," Computer Aided Surgery, 8(1):17-23 (2003).

(56) References Cited

OTHER PUBLICATIONS

Liu, Yanfeng et al., "Human-Readable Fiducial Marker Classification using Convolutional Neural Networks," 2017 IEEE International Conference on Electro Information Technology (EIT), IEEE, May 14, 2017, 5 pages.
Lootus, M. et al., "Vertebrae Detection and Labelling in Lumbar MR Images," Jan. 1, 2014, 12 pages.
Shi, R. et al., "An Efficient Method for Segmentation of MRI Spine Images," IEEE/ICME International Conference on Complex Medical Engineering, Jun. 2007, 6 pages; doi:10.1109/ICCME.2007.4381830.
Song, Yuheng & Hao, Yan, "Image Segmentation Algorithms Overview," Jul. 7, 2017, retrieved from the Internet at: https://arxiv.org/ftp/arxiv/papers/1707/1707.02051, 6 pages.
Yang, D. et al., "Deep Image-to-Image Recurrent Network with Shape Basis Learning for Automatic Vertebra Labeling in Large-Scale 3D CT Volumes," Conference: International Conference on Medical Image Computing and Computer-Assisted Intervention, doi:10.1007/978-3-319-66179-7_57, Sep. 2017, 9 pages.
Non-Final Office Action dated Mar. 25, 2021 for U.S. Appl. No. 16/217,061, 25 pages.
Non-Final Office Action dated Jan. 31, 2022 for U.S. Appl. No. 17/145,178, 25 pages.
Final Office Action dated Jun. 24, 2021 for U.S. Appl. No. 16/101,459, 40 pages.
Non-Final Office Action dated Oct. 4, 2021 for U.S. Appl. No. 17/145,178, 22 pages.
Final Office Action dated Oct. 4, 2021 for U.S. Appl. No. 16/217,061, 68 pages.
Non-Final Office Action dated Dec. 21, 2021 for U.S. Appl. No. 16/236,663, 32 pages.
Non-Final Office Action dated Apr. 28, 2021 for U.S. Appl. No. 16/217,073, 12 pages.
Final Office Action dated Jun. 15, 2021 for U.S. Appl. No. 16/537,645, 13 pages.
Esfandiari, H. et al., "A deep learning framework for segmentation and pose estimation of pedicle screw implants based on C-arm fluoroscopy," International Journal of Computer Assisted Radiology and Surgery, 13:1269-1282 (2018).

* cited by examiner

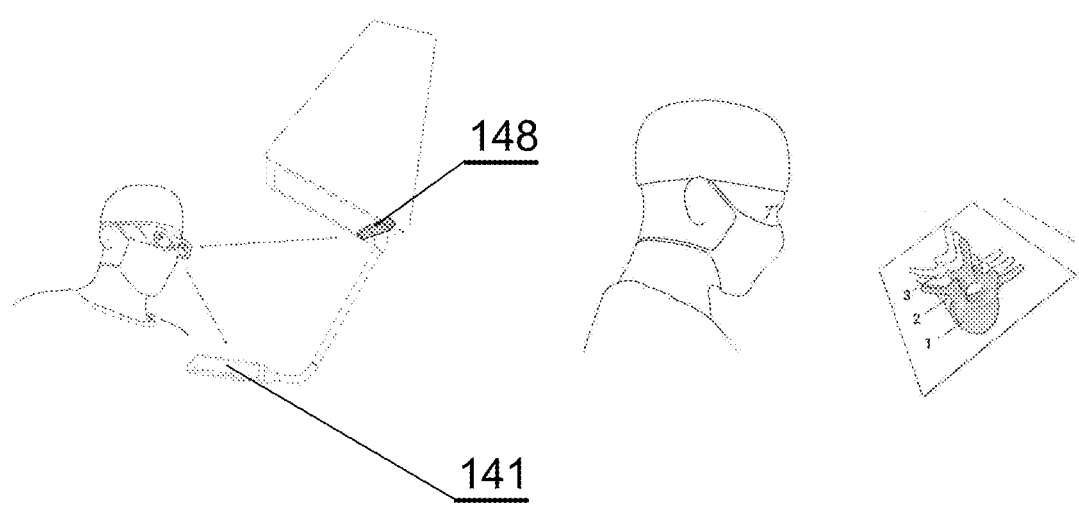
Fig. 5A                                   Fig. 5B

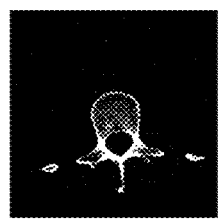  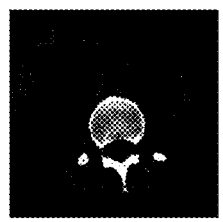 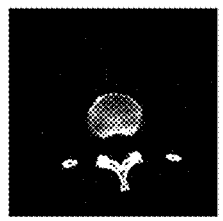 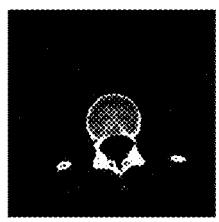
Fig. 7A  Fig. 7B  Fig. 7C  Fig. 7D  Fig. 7E
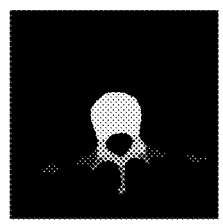  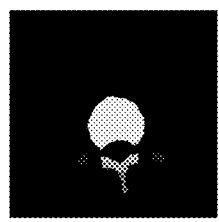 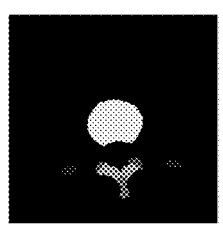 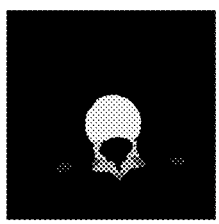
Fig. 7F  Fig. 7G  Fig. 7H  Fig. 7I  Fig. 7J
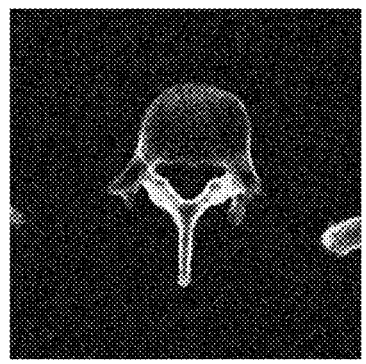 
Fig. 8A  Fig. 8B
 
Fig. 8C  Fig. 8D

GRAPHICAL USER INTERFACE FOR DISPLAYING AUTOMATICALLY SEGMENTED INDIVIDUAL PARTS OF ANATOMY IN A SURGICAL NAVIGATION SYSTEM

TECHNICAL FIELD

The present disclosure relates to graphical user interfaces for surgical navigation systems, in particular to a system and method for operative planning and real time execution of a surgical procedure including displaying automatically segmented individual parts of the patient anatomy.

BACKGROUND

Some of typical functions of a computer-assisted surgery (CAS) system with navigation include presurgical planning of a procedure and presenting preoperative diagnostic information and images in useful formats. The CAS system presents status information about a procedure as it takes place in real time, displaying the preoperative plan along with intraoperative data. The CAS system may be used for procedures in traditional operating rooms, interventional radiology suites, mobile operating rooms or outpatient clinics. The procedure may be any medical procedure, whether surgical or non-surgical.

Surgical navigation systems are used to display the position and orientation of surgical instruments and medical implants with respect to presurgical or intraoperative medical imagery datasets of a patient. These images include pre and intraoperative images, such as two-dimensional (2D) fluoroscopic images and three-dimensional (3D) magnetic resonance imaging (MRI) or computed tomography (CT).

Navigation systems locate markers attached or fixed to an object, such as surgical instruments and patient. Most commonly these tracking systems are optical and electro-magnetic. Optical tracking systems have one or more stationary cameras that observe passive reflective markers or active infrared LEDs attached to the tracked instruments or the patient. Eye-tracking solutions are specialized optical tracking systems that measure gaze and eye motion relative to a user's head. Electro-magnetic systems have a stationary field generator that emits an electromagnetic field that is sensed by coils integrated into tracked medical tools and surgical instruments.

SUMMARY OF THE INVENTION

Incorporating image segmentation processes that automatically identify various bone landmarks, based on their density, can increase planning accuracy. One such bone landmark is the spinal pedicle, which is made up of dense cortical bone making its identification utilizing image segmentation easier. The pedicle is used as an anchor point for various types of medical implants. Achieving proper implant placement in the pedicle is heavily dependent on the trajectory selected for implant placement. Ideal trajectory is identified by surgeon based on review of advanced imaging (e.g., CT or MRI), goals of the surgical procedure, bone density, presence or absence of deformity, anomaly, prior surgery, and other factors. The surgeon then selects the appropriate trajectory for each spinal level. Proper trajectory generally involves placing an appropriately sized implant in the center of a pedicle. Ideal trajectories are also critical for placement of inter-vertebral biomechanical devices.

Another example is placement of electrodes in the thalamus for the treatment of functional disorders, such as Parkinson's. The most important determinant of success in patients undergoing deep brain stimulation surgery is the optimal placement of the electrode. Proper trajectory is defined based on preoperative imaging (such as MRI or CT) and allows for proper electrode positioning.

Another example is minimally invasive replacement of prosthetic/biologic mitral valve in for the treatment of mitral valve disorders, such as mitral valve stenosis or regurgitation. The most important determinant of success in patients undergoing minimally invasive mitral valve surgery is the optimal placement of the three dimensional valve.

The fundamental limitation of surgical navigation systems is that they provide restricted means of communicating to the surgeon. Currently-available navigation systems present some drawbacks.

Typically, one or several computer monitors are placed at some distance away from the surgical field. They require the surgeon to focus the visual attention away from the surgical field to see the monitors across the operating room. This results in a disruption of surgical workflow. Moreover, the monitors of current navigation systems are limited to displaying multiple slices through three-dimensional diagnostic image datasets, which are difficult to interpret for complex 3D anatomy.

The fact that the screen of the surgical navigation system is located away from the region of interest (ROI) of the surgical field requires the surgeon to continuously look back and forth between the screen and the ROI. This task is not intuitive and results in a disruption to surgical workflow and decreases planning accuracy.

When defining and later executing an operative plan, the surgeon interacts with the navigation system via a keyboard and mouse, touchscreen, voice commands, control pendant, foot pedals, haptic devices, and tracked surgical instruments. Based on the complexity of the 3D anatomy, it can be difficult to simultaneously position and orient the instrument in the 3D surgical field only based on the information displayed on the monitors of the navigation system. Similarly, when aligning a tracked instrument with an operative plan, it is difficult to control the 3D position and orientation of the instrument with respect to the patient anatomy. This can result in an unacceptable degree of error in the preoperative plan that will translate to poor surgical outcome.

One aspect of the invention is a surgical navigation system comprising: a source of a patient anatomy data; wherein the patient anatomy data comprises a three-dimensional reconstruction of a segmented model comprising at least two sections representing parts of the anatomy; a surgical navigation image generator configured to generate a surgical navigation image comprising the patient anatomy; a 3D display system configured to show the surgical navigation image wherein the display of the patient anatomy is selectively configurable such that at least one section of the anatomy is displayed and at least one other section of the anatomy is not displayed.

The system may further comprise a tracking system for real-time tracking of: a surgeon's head, a see-through visor of the 3D display system and a patient anatomy to provide current position and/or orientation data; wherein the surgical navigation image generator is configured to generate the surgical navigation image in accordance to the current position and/or orientation data provided by the tracking system.

The system may further comprise a source of at least one of: an operative plan and a virtual surgical instrument model;

wherein the tracking system is further configured for real-time tracking of surgical instruments; wherein the surgical navigation image further comprises a three-dimensional image representing a virtual image of the surgical instruments.

The virtual image of the surgical instruments can be configured to indicate the suggested positions and/or orientations of the surgical instruments according to the operative plan data.

The three-dimensional image of the surgical navigation image may further comprise a graphical cue indicating the required change of position and/or orientation of the surgical instrument to match the suggested position and/or orientation according to the pre-operative plan data.

The surgical navigation image may further comprise a set of orthogonal (axial, sagittal, and coronal) and/or arbitrary planes of the patient anatomy data.

The 3D display system may comprise a 3D projector for projecting the surgical navigation image onto a see-through projection screen, which is partially transparent and partially reflective, for showing the surgical navigation image.

The 3D display system may comprise a 3D projector for projecting the surgical navigation image onto an opaque projection screen for showing the surgical navigation image for emission towards the see-through mirror, which is partially transparent and partially reflective.

The 3D display may comprise a 3D projector for projecting the surgical navigation image towards a plurality of opaque mirrors for reflecting the surgical navigation image towards an opaque projection screen for showing the surgical navigation image for emission towards the see-through mirror, which is partially transparent and partially reflective.

The 3D display may comprise a 3D monitor for showing the surgical navigation image for emission towards the see-through mirror which is partially transparent and partially reflective.

The 3D display may comprise a see-through 3D screen, which is partially transparent and partially emissive, for showing the surgical navigation image.

The see-through visor can be configured to be positioned, when the system is in use, at a distance from the surgeon's head which is shorter than the distance from the surgical field of the patient anatomy.

The surgical navigation image generator can be controllable by an input interface comprising at least one of: foot-operable pedals, a microphone, a joystick, an eye-tracker.

The tracking system may comprise plurality of arranged fiducial markers, including a head array, a display array, a patient anatomy array, an instrument array; and a fiducial marker tracker configured to determine in real time the positions and orientations of each of the components of the surgical navigation system.

At least one of the head array, the display array, the patient anatomy array, the instrument array may contain several fiducial markers that are not all coplanar.

The patient anatomy data may comprise output data of a semantic segmentation process of an anatomy scan image.

The system may further comprise a convolutional neural network system configured to perform the semantic segmentation process to generate the patient anatomy data.

The convolutional neural network (CNN) system may comprise: at least one non-transitory processor-readable storage medium that stores at least one of processor-executable instructions or data; and at least one processor communicably coupled to at least one non-transitory processor-readable storage medium, wherein that at least one processor: receives segmentation learning data comprising a plurality of batches of labeled anatomical image sets, each image set comprising image data representative of a series of slices of a three-dimensional bony structure of the anatomy, and each image set including at least one label which identifies the region of a particular part of the bony structure depicted in each image of the image set, wherein the label indicates one of a plurality of classes indicating parts of the bone anatomy; trains a segmentation CNN, that is a fully convolutional neural network model with layer skip connections to segment semantically at least one part of the bony structure utilizing the received segmentation learning data; and stores the trained segmentation CNN in at least one non-transitory processor-readable storage medium of the machine learning system.

Training the CNN model may include training a CNN model including a contracting path and an expanding path. The contracting path may include a number of convolutional layers, a number of pooling layers and dropout layers. Each pooling and dropout layer may be preceded by at least one convolutional layer. The expanding path may include a number of convolutional layers, a number of upsampling layers and a concatenation of feature maps from previous layers. Each upsampling layer may be preceded by at least one convolutional layer and may include a transpose convolution operation which performs upsampling and interpolation with a learned kernel.

Training a CNN model may include training a CNN model to segment at least one part of the anatomical structure utilizing the received learning data and, subsequent to each upsampling layer, the CNN model may include a concatenation of feature maps from a corresponding layer in the contracting path through a skip connection. Receiving learning data may include receiving preoperative or intra-operative images of the bony structure. Training a CNN model may include training a CNN model to segment at least one part of the anatomical structure utilizing the received learning data, and the CNN model may include a contracting path which may include a first convolutional layer, which may have between 1 and 256 feature maps. Training a CNN model may include training a CNN model which may include a plurality of convolutional layers to segment at least one part of the anatomical structure of the vertebrae utilizing the received learning data, and each convolutional layer may include a convolutional kernel of sizes 2n+1×2n+1, with n being a natural number, and a selectable stride. Training a CNN model may include training a CNN model which may include a plurality of pooling layers to segment at least one part of the anatomical structure utilizing the received learning data, and each pooling layer may include an n×n maximum or other type of pooling, with a selectable stride, with n being a natural number.

A CNN model may include training a CNN model to segment at least one part of the anatomical structure utilizing the received learning data, and the CNN model may include a plurality of pooling layers and a plurality of upsampling layers.

A CNN model may include training a CNN model which may include a plurality of convolutional layers to segment at least one part of the anatomical structure utilizing the received learning data, and the CNN model may pad the input to each convolutional layer using a zero padding operation.

A CNN model may include training a CNN model to segment at least one part of the anatomical structure utilizing the received learning data, and the CNN model may include a plurality of nonlinear activation function layers. The method may further include augmenting, by at least one processor, the learning data via modification of at least some of the image data in the plurality of batches of labeled image sets.

The method may further include modifying, by at least one processor, at least some of the image data in the plurality of batches of labeled image sets according to at least one of: a horizontal flip, a vertical flip, a shear amount, a shift amount, a zoom amount, a rotation amount, a brightness level, or a contrast level, additive noise of Gaussian and/or Poisson distribution and Gaussian blur.

The CNN model may include a plurality of hyperparameters stored in at least one non-transitory processor-readable storage medium, and may further include configuring, by at least one processor, the CNN model according to a plurality of configurations; for each of the plurality of configurations, validating, by at least one processor, the accuracy of the CNN model; and selecting, by at least one processor, at least one configuration based at least in part on the accuracies determined by the validations.

The method may further include for each image set, identifying, by at least one processor, whether the image set is missing a label for any of a plurality of parts of the anatomical structure; and for image sets identified as missing at least one label, modifying, by at least one processor, a training loss function to account for the identified missing labels. Receiving learning data may include receiving image data which may include volumetric images, and each label may include a volumetric label mask or contour.

A CNN model may include training a CNN model which may include a plurality of convolutional layers to segment at least one part of the anatomical structure utilizing the received learning data, and each convolutional layer of the CNN model may include a convolutional kernel of size N×N×K pixels, where N and K are positive integers.

A CNN model may include training a CNN model which may include a plurality of convolutional layers to segment at least one part of the anatomical structure utilizing the received learning data, and each convolutional layer of the CNN model may include a convolutional kernel of size N×M pixels, where N and M are positive integers. Receiving learning data may include receiving image data representative of labeled anatomical parts. Training a CNN model may include training a CNN model to segment at least one part of the anatomical structure utilizing the received learning data, and for each processed image, the CNN model may utilize data for at least one image which is at least one of: adjacent to the processed image with respect to space A method of operating a machine learning system may include at least one non-transitory processor-readable storage medium that stores at least one of processor-executable instructions or data, and at least one processor communicably coupled to at least one non-transitory processor-readable storage medium. The method may be summarized as including receiving, by at least one processor, image data which represents an anatomical structure; processing, by at least one processor, the received image data through a fully convolutional neural network (CNN) model to generate per-class probabilities for each pixel of each image of the image data, each class corresponding to one of a plurality of parts of the anatomical structure represented by the image data; and for each image of the image data, generating, by at least one processor, a probability map for each of the plurality of classes using the generated per-class probabilities; and storing, by at least one processor, the generated probability maps in at least one non-transitory processor-readable storage medium.

Processing the received image data through the CNN model may include processing the received image data through a CNN model which may include a contracting path and an expanding path. The contracting path may include a number of convolutional layers and a number of pooling layers, each pooling layer preceded by at least one convolutional layer. The expanding path may include a number of convolutional layers and a number of upsampling layers, each upsampling layer preceded by at least one convolutional layer, and may include a transpose convolution operation which performs upsampling and interpolation with a learned kernel. Receiving image data may include, for example, receiving image data that is representative of a vertebrae in a spine. The method may further include autonomously causing, by the at least one processor, an indication of at least one of the plurality of parts of the anatomical structure to be displayed on a display based at least in part on the generated probability maps.

The method may further include post-processing, by at least one processor, the processed image data to ensure at least one physical constraint is met. Receiving image data may include, for example, receiving image data that may be representative of vertebrae, and at least one physical constraint may include at least one of: constraints on the volumes of anatomical parts of the bony structure, such as a spine, coincidence and connections of the anatomical parts of the vertebrae, such as the vertebral body must be connected to two pedicles, spinous process must be connected to the lamina and cannot be connected to the vertebral body etc.

The method may further include for each image of the image data, transforming, by at least one processor, the plurality of probability maps into a label mask by setting the class of each pixel to the class with the highest probability.

The method may further include for each image of the image data, setting, by at least one processor, the class of each pixel to a background class when all of the class probabilities for the pixel are below a determined threshold.

The method may further include for each image of the image data, setting, by at least one processor, the class of each pixel to a background class when the pixel is not part of a largest connected region for the class to which the pixel is associated.

The method may further include converting, by at least one processor, each of the label masks for the image data combined into a 3D volume and further converting it into an alternative representation in the form of a polygonal mesh.

The method may further include autonomously causing, by at least one processor, the generated mesh to be displayed with the image data on a display.

The method may further include receiving, by at least one processor, a user modification of at least one of the displayed volumes and/or meshes in terms of change of color, opacity, changing the mesh decimation; and storing, by at least one processor, the modified volumes and/or meshes in at least one non-transitory processor-readable storage medium. The method may further include determining, by at least one processor, the volume of at least one of the plurality of parts of the anatomical structure utilizing the generated volume or mesh.

The method may further include causing, by at least one processor, the determined volume of at least one of the plurality of parts of the anatomical structure to be displayed on a display. Receiving image data may include receiving volumetric image data or polygonal mesh data. Processing the received image data through a CNN model may include processing the received image data through a CNN model in which each convolutional layer may include a convolutional kernel of sizes N×N×K pixels, where N and K are positive integers.

Another aspect of the invention is a method for providing an augmented reality image during an operation, comprising: providing a source of a patient anatomy data; wherein the patient anatomy data comprises a three-dimensional reconstruction of a segmented model comprising at least two sections representing parts of the anatomy; generating, by a surgical navigation image generator, a surgical navigation image comprising the patient anatomy; showing the surgical navigation image at 3D display system and configuring the display of the patient anatomy such that at least one section of the anatomy is displayed and at least one other section of the anatomy is not displayed.

These and other features, aspects and advantages of the invention will become better understood with reference to the following drawings, descriptions and claims.

BRIEF DESCRIPTION OF FIGURES

Various embodiments are herein described, by way of example only, with reference to the accompanying drawings, wherein:

FIG. 5A shows eye tracking in accordance with an embodiment of the invention;

FIG. 5B shows eye tracking in accordance with an embodiment of the invention;

FIG. 7A shows an example of a CT image of a spine;

FIG. 7B shows another example of a CT image of a spine;

FIG. 7C shows another example of a CT image of a spine;

FIG. 7D shows another example of a CT image of a spine;

FIG. 7E shows another example of a CT image of a spine;

FIG. 7F shows a semantic segmented image corresponding to the CT image of FIG. 7A, in accordance with an embodiment of the invention;

FIG. 7G shows a semantic segmented image corresponding to the CT image of FIG. 7B, in accordance with an embodiment of the invention;

FIG. 7H shows a semantic segmented image corresponding to the CT image of FIG. 7C, in accordance with an embodiment of the invention;

FIG. 7I shows a semantic segmented image corresponding to the CT image of FIG. 7D, in accordance with an embodiment of the invention;

FIG. 7J shows a semantic segmented image corresponding to the CT image of FIG. 7E, in accordance with an embodiment of the invention;

FIG. 8A shows an enlarged view of a LDCT scan;

FIG. 8B shows an enlarged view of a HDCT scan;

FIG. 8C shows a low power magnetic resonance scan of a neck portion;

FIG. 8D shows a higher power magnetic resonance scan of the same neck portion as FIG. 8C;

DETAILED DESCRIPTION OF THE INVENTION

The following detailed description is of the best currently contemplated modes of carrying out the invention. The description is not to be taken in a limiting sense, but is made merely for the purpose of illustrating the general principles of the invention.

Figure 1A:
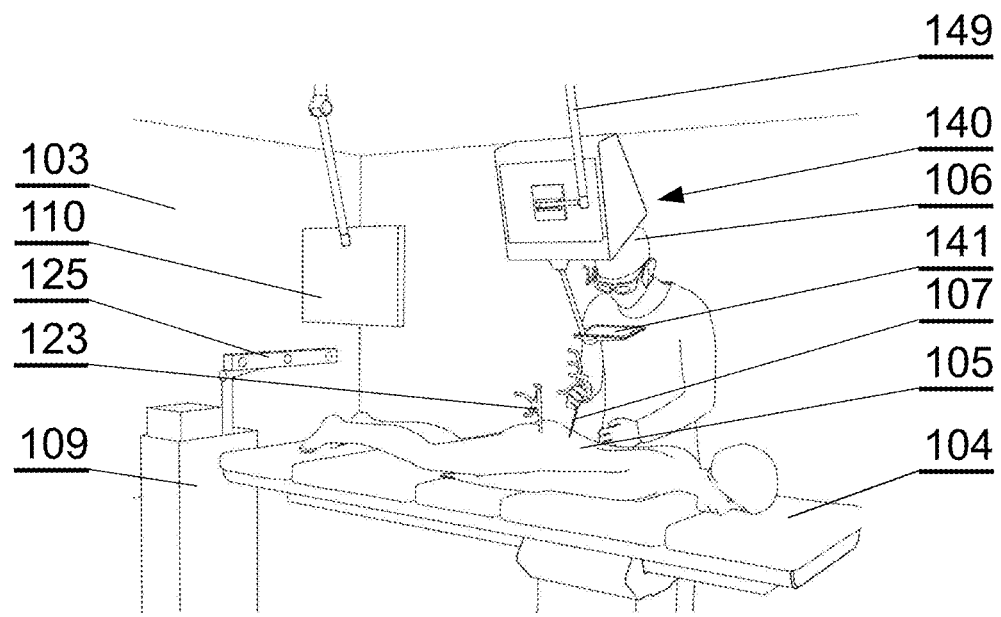
FIG. 1A shows a layout of a surgical room employing the surgical navigation system in accordance with an embodiment of the invention.
Figures 1B, 1C:
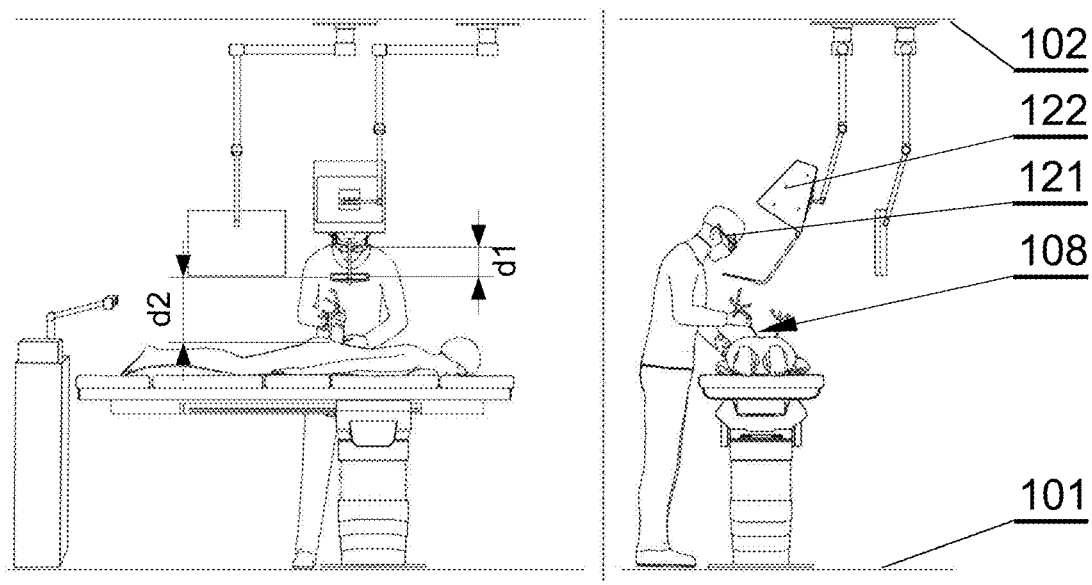
FIG. 1B shows a layout of a surgical room employing the surgical navigation system in accordance with an embodiment of the invention.
FIG. 1C shows a layout of a surgical room employing the surgical navigation system in accordance with an embodiment of the invention.

The system presented herein, in accordance with one embodiment, comprises a 3D display system 140 to be implemented directly on real surgical applications in a surgical room as shown in FIGS. 1A-1C. The 3D display system 140 as shown in the embodiment of FIGS. 1A-1C comprises a 3D display 142 for emitting a surgical navigation image 142A towards a see-through mirror 141 that is partially transparent and partially reflective, such that an augmented reality image 141A collocated with the patient anatomy in the surgical field 108 underneath the see-through mirror 141 is visible to a viewer looking from above the see-through mirror 141 towards the surgical field 108.

The surgical room typically comprises a floor 101 on which an operating table 104 is positioned. A patient 105 lies on the operating table 104 while being operated by a surgeon 106 with the use of various surgical instruments 107. The surgical navigation system as described in details below can have its components, in particular the 3D display system 140, mounted to a ceiling 102, or alternatively to the floor 101 or a side wall 103 of the operating room. Furthermore, the components, in particular the 3D display system 140, can be mounted to an adjustable and/or movable floor-supported structure (such as a tripod). Components other than the 3D display system 140, such as the surgical image generator 131, can be implemented in a dedicated computing device 109, such as a stand-alone PC computer, which may have its own input controllers and display(s) 110.

In general, the system is designed for use in such a configuration wherein the distance d1 between the surgeon's eyes and the see-through mirror 141, is shorter than the distance d2, between the see-through mirror 141 and the operative field at the patient anatomy 105 being operated.

Figure 2A:
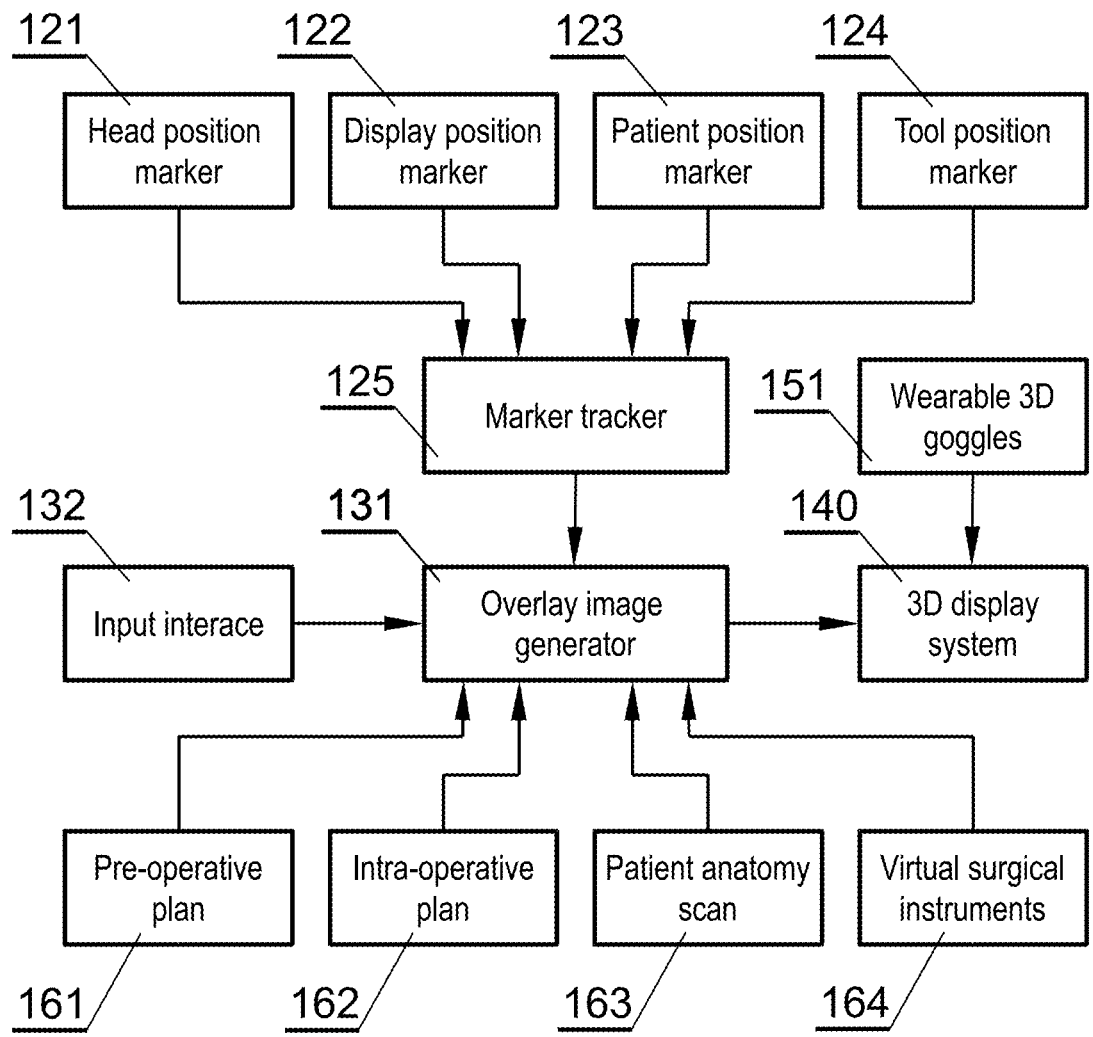
FIG. 2A shows the connections between the different components that interact in accordance with an embodiment of the invention.
Figure 2B:
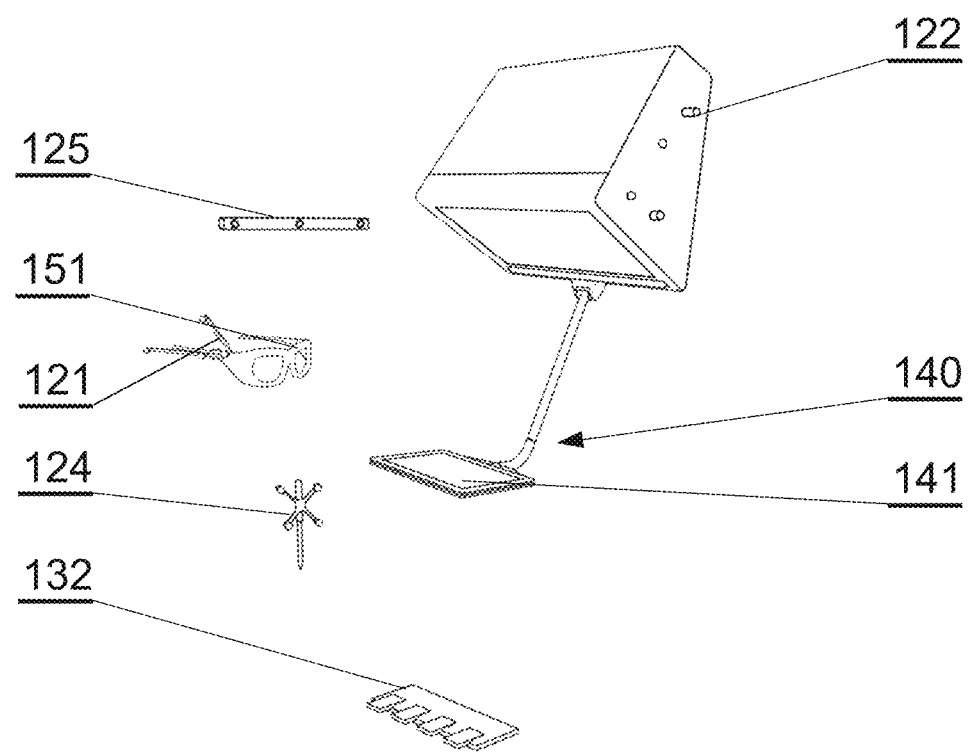
FIG. 2B shows components of the surgical navigation system in accordance with an embodiment of the invention.

FIG. 2A shows a functional schematic presenting connections between the components of the surgical navigation system and FIG. 2B shows examples of physical embodiments of various components.

The surgical navigation system comprises a tracking system for tracking in real time the position and/or orientation of various entities to provide current position and/or orientation data. For example, the system may comprise a plurality of arranged fiducial markers, which are trackable by a fiducial marker tracker 125. Any known type of tracking system can be used, for example in case of a marker tracking system, 4-point marker arrays are tracked by a three-camera sensor to provide movement along six degrees of freedom. A head position marker array 121 can be attached to the surgeon's head for tracking of the position and orientation of the surgeon and the direction of gaze of the surgeon—for example, the head position marker array 121 can be integrated with the wearable 3D glasses 151 or can be attached to a strip worn over surgeon's head.

A display marker array 122 can be attached to the see-through mirror 141 of the 3D display system 140 for tracking its position and orientation, as the see-through mirror 141 is movable and can be placed according to the current needs of the operative setup.

A patient anatomy marker array 123 can be attached at a particular position and orientation of the anatomy of the patient.

A surgical instrument marker array 124 can be attached to the instrument whose position and orientation shall be tracked.

Preferably, the markers in at least one of the marker arrays 121-124 are not coplanar, which helps to improve the accuracy of the tracking system.

Therefore, the tracking system comprises means for real-time tracking of the position and orientation of at least one of: a surgeon's head 106, a 3D display 142, a patient anatomy 105, and surgical instruments 107. Preferably, all of these elements are tracked by a fiducial marker tracker 125.

A surgical navigation image generator 131 is configured to generate an image to be viewed via the see-through mirror 141 of the 3D display system. It generates a surgical navigation image 142A comprising data of at least one of: the pre-operative plan 161 (which are generated and stored in a database before the operation), data of the intra-operative plan 162 (which can be generated live during the operation), data of the patient anatomy scan 163 (which can be generated before the operation or live during the operation) and virtual images 164 of surgical instruments used during the operation (which are stored as 3D models in a database).

The surgical navigation image generator 131, as well as other components of the system, can be controlled by a user (i.e. a surgeon or support staff) by one or more user interfaces 132, such as foot-operable pedals (which are convenient to be operated by the surgeon), a keyboard, a mouse, a joystick, a button, a switch, an audio interface (such as a microphone), a gesture interface, a gaze detecting interface etc. The input interface(s) are for inputting instructions and/or commands.

All system components are controlled by one or more computer which is controlled by an operating system and one or more software applications. The computer may be equipped with a suitable memory which may store computer program or programs executed by the computer in order to execute steps of the methods utilized in the system. Computer programs are preferably stored on a non-transitory medium. An example of a non-transitory medium is a non-volatile memory, for example a flash memory while an example of a volatile memory is RAM. The computer instructions are executed by a processor. These memories are exemplary recording media for storing computer programs comprising computer-executable instructions performing all the steps of the computer-implemented method according the technical concept presented herein. The computer(s) can be placed within the operating room or outside the operating room. Communication between the computers and the components of the system may be performed by wire or wirelessly, according to known communication means.

The aim of the system is to generate, via the 3D display system 140, an augmented reality image such as shown in examples of FIGS. 3F-3I and also possibly 3A-3E. When the surgeon looks via the 3D display system 140, the surgeon sees the augmented reality image 141A which comprises:
 the real world image: the patient anatomy, surgeon's hands and the instrument currently in use (which may be partially inserted into the patient's body and hidden under the skin);
 and a computer-generated surgical navigation image 142A comprising the patient anatomy 163 configurable such that at least one section of the anatomy 163A-163F is displayed and at least one other section of the anatomy 163A-163F is not displayed.

Figure 3A:
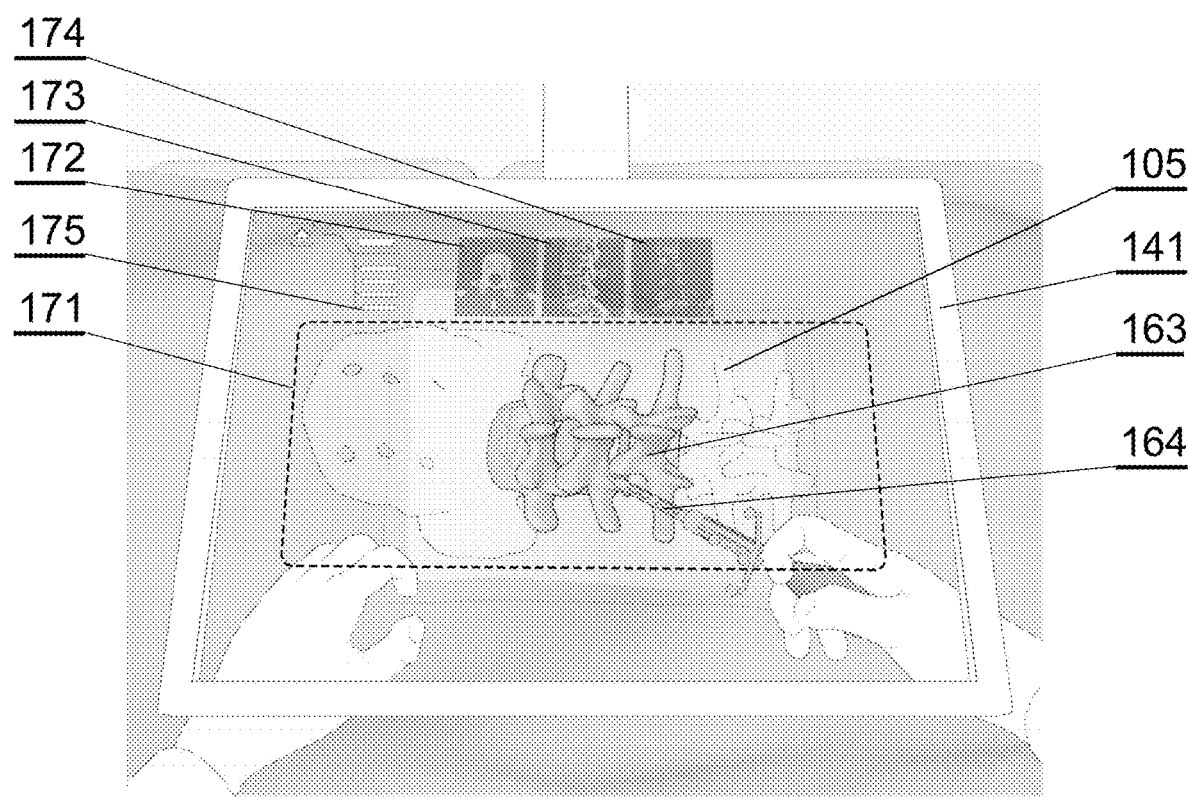
FIG. 3A shows an example of an augmented reality display in accordance with an embodiment of the invention.
Figure 3B:
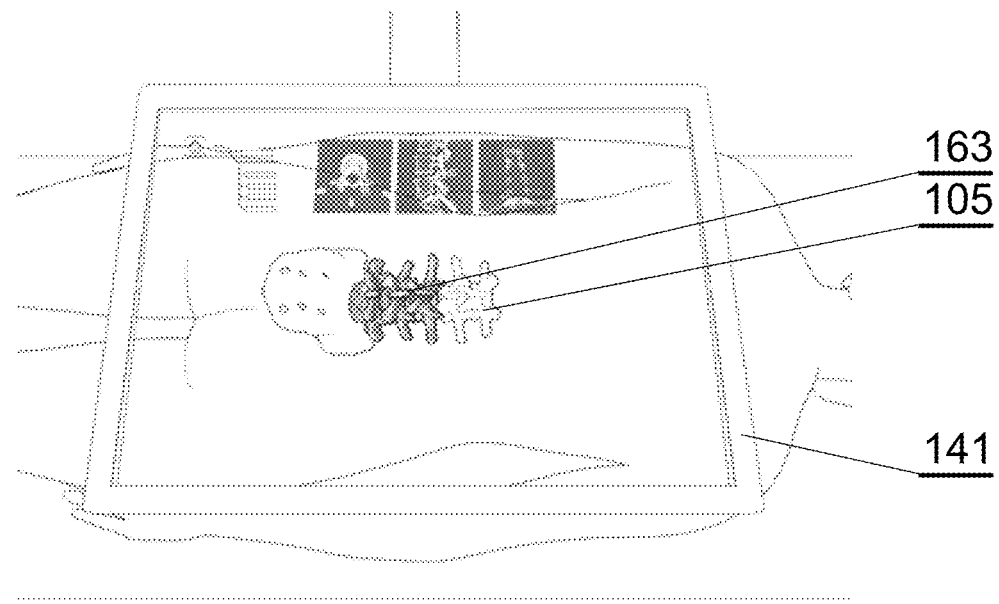
FIG. 3B shows an example of an augmented reality display in accordance with an embodiment of the invention.
Figure 3C:
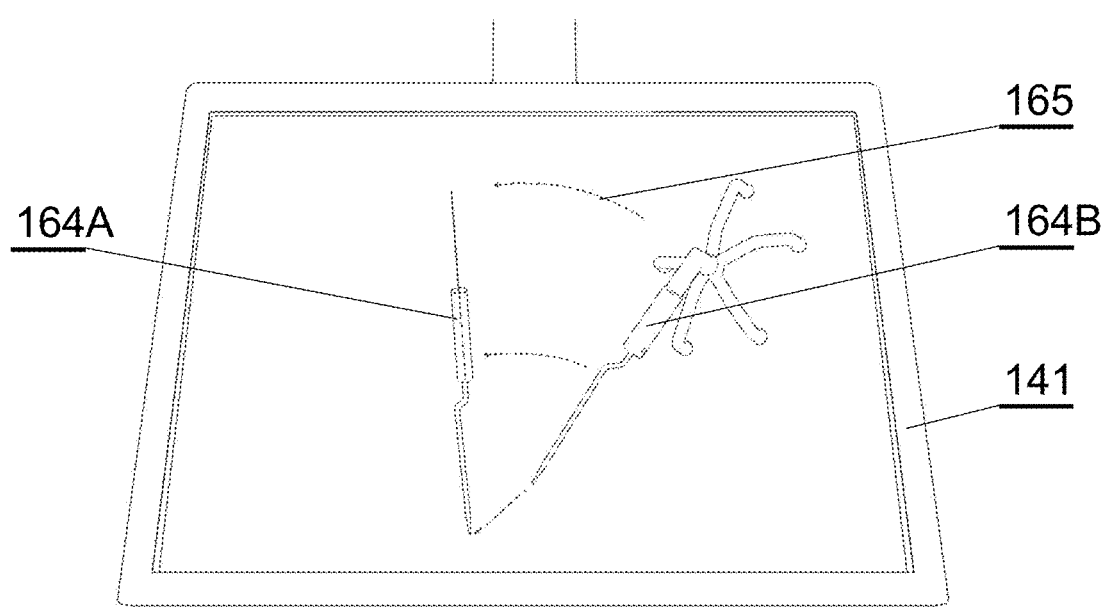
FIG. 3C shows an example of an augmented reality display in accordance with an embodiment of the invention.

Furthermore, the surgical navigation image may further comprise a 3D image 171 representing at least one of: the virtual image of the instrument 164 or surgical guidance indicating suggested (ideal) trajectory and placement of surgical instruments 107, according to the pre-operative plans 161 (as shown in FIG. 3C); preferably, three different orthogonal planes of the patient anatomy data 163: coronal 174, sagittal 173, axial 172; preferably, a menu 175 for controlling the system operation.

If the 3D display 142 is stereoscopic, the surgeon shall use a pair of 3D glasses 151 to view the augmented reality image 141A. However, if the 3D display 142 is autostereoscopic, it may be not necessary for the surgeon to use the 3D glasses 151 to view the augmented reality image 141A.

The virtual image of the patient anatomy 163 is generated based on data representing a three-dimensional segmented model comprising at least two sections representing parts of the anatomy. The anatomy can be for example a bone structure, such as a spine, skull, pelvis, long bones, shoulder joint, hip joint, knee joint etc. This description presents examples related particularly to a spine, but a skilled person will realize how to adapt the embodiments to be applicable to the other bony structures or other anatomy parts as well.

Figure 6:
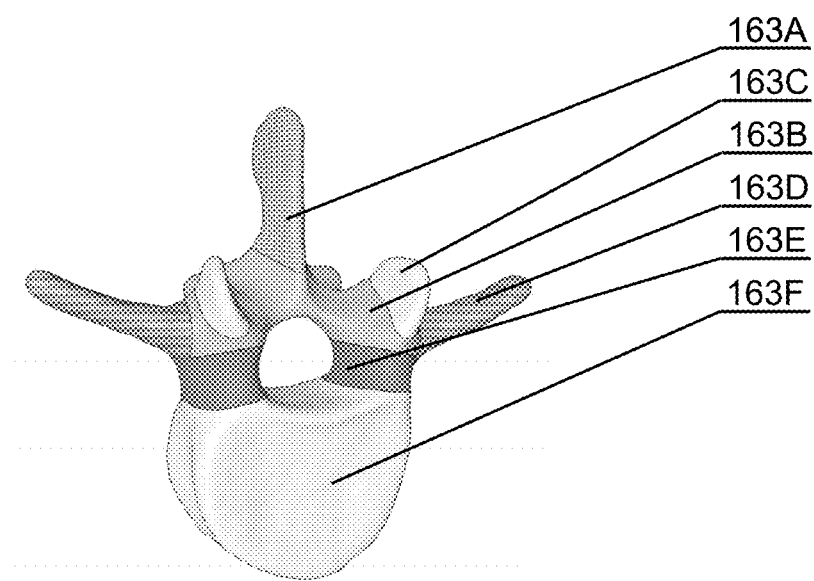
FIG. 6 shows a 3D representation of the results of the semantic segmentation on one vertebrae in accordance with an embodiment of the invention.
Figure 9:
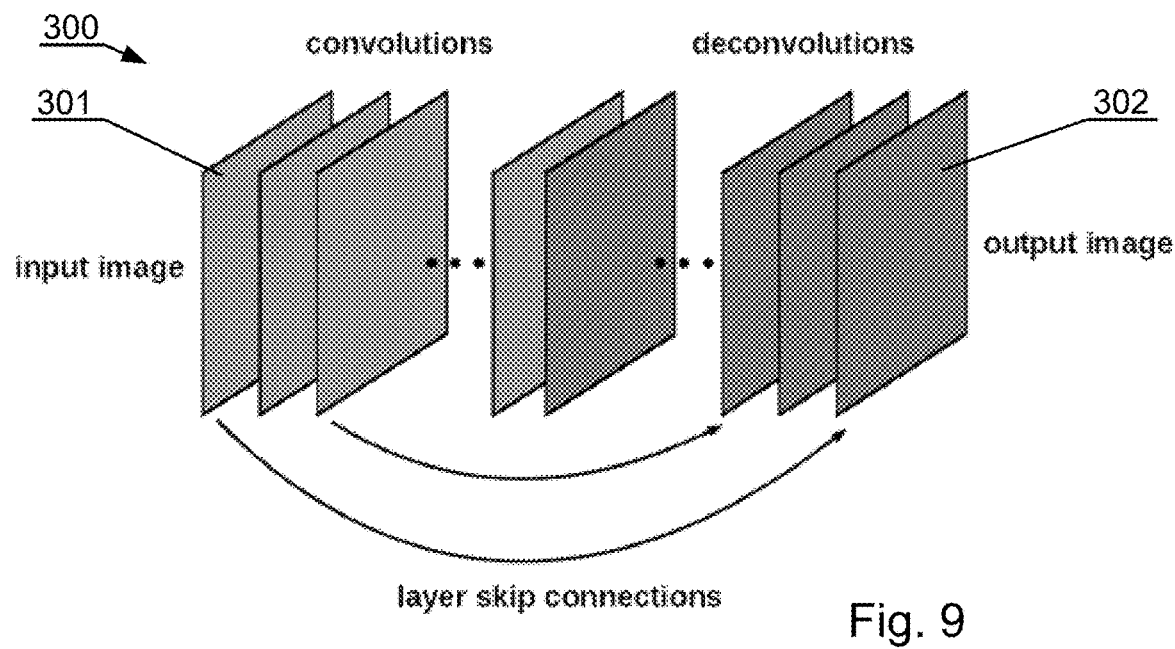
FIG. 9 shows a denoising CNN architecture in accordance with an embodiment of the invention.

For example, the model can represent a spine, as shown in FIG. 6, with the following section: spinous process 163A, lamina 163B, articular process 163C, transverse process 163D, pedicles 163E, vertebral body 163F.

The model can be generated based on a pre-operative scan of the patient and then segmented manually by a user or automatically by a computer, using dedicated algorithms and/or neural networks, or in a hybrid approach including a computer-assisted manual segmentation. For example, a convolutional neural network such as explained with reference to FIGS. 7-14 can be employed.

Preferably, the images of the orthogonal planes 172, 173, 174 are displayed in an area next (preferably, above) to the area of the 3D image 171, as shown in FIG. 3A, wherein the 3D image 171 occupies more than 50% of the area of the see-through visor 141.

The location of the images of the orthogonal planes 172, 173, 174 may be adjusted in real time depending on the location of the 3D image 171, when the surgeon changes the position of the head during operation, such as not to interfere with the 3D image 171.

Therefore, in general, the anatomical information of the user is shown in two different layouts that merge for an augmented and mixed reality feature. The first layout is the anatomical information that is projected in 3D in the surgical field. The second layout is in the orthogonal planes.

The surgical navigation image 142A is generated by the image generator 131 in accordance with the tracking data provided by the fiducial marker tracker 125, in order to superimpose the anatomy images and the instrument images exactly over the real objects, in accordance with the position and orientation of the surgeon's head. The markers are tracked in real time and the image is generated in real time. Therefore, the surgical navigation image generator 131 provides graphics rendering of the virtual objects (patient anatomy, surgical plan and instruments) collocated to the real objects according to the perspective of the surgeon's perspective.

For example, surgical guidance may relate to suggestions (virtual guidance clues 164) for placement of a pedicle screw in spine surgery or the ideal orientation of an acetabular component in hip arthroplasty surgery. These suggestions may take a form of animations that show the surgeon whether the placement is correct. The suggestions may be displayed both on the 3D holographic display and the orthogonal planes. The surgeon may use the system to plan these orientations before or during the surgical procedure.

In particular, the 3D image 171 is adapted in real time to the position and orientation of the surgeon's head. The display of the different orthogonal planes 172, 173, 174 may be adapted according to the current position and orientation of the surgical instruments used.

FIG. 3B shows an example indicating collocation of the virtual image of the patient anatomy 163 and the real anatomy 105.

For example, as shown in FIG. 3C, the 3D image 171 may demonstrate a mismatch between a supposed/suggested position of the instrument according to the pre-operative plan 161, displayed as a first virtual image of the instrument 164A located at its supposed/suggested position, and an actual position of the instrument, visible either as the real instrument via the see-through display and/or a second virtual image of the instrument 164B overlaid on the current position of the instrument. Additionally, graphical guiding cues, such as arrows 165 indicating the direction of the supposed change of position, can be displayed.

Figure 3D:
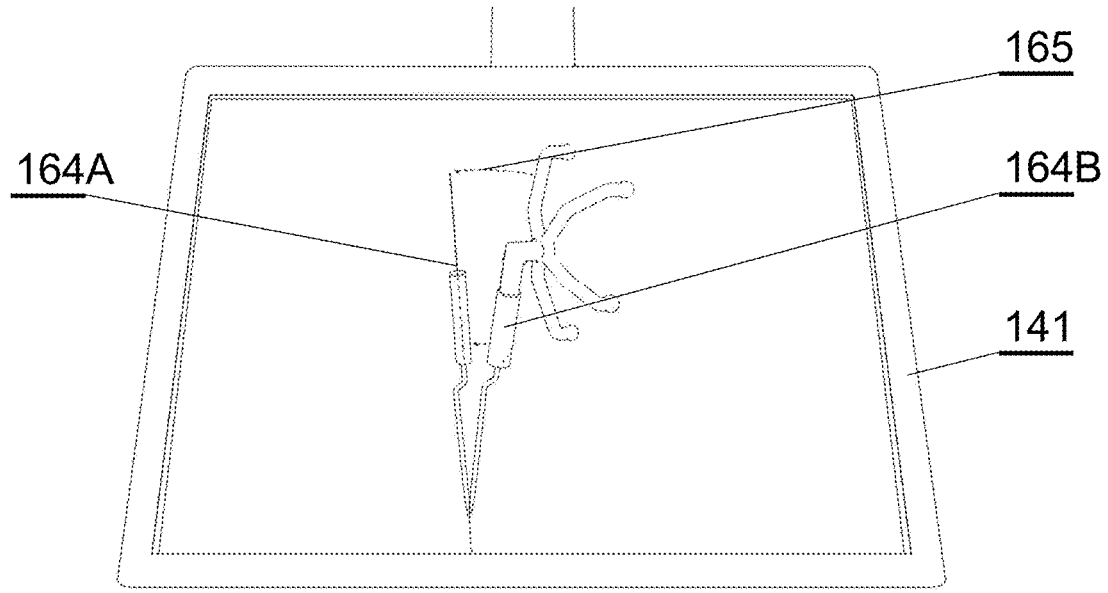
FIG. 3D shows an example of an augmented reality display in accordance with an embodiment of the invention.

FIG. 3D shows a situation wherein the tip of the supposed position of the instrument displayed as the first virtual image 164A according to the pre-operative plan 161 matches the tip of the real surgical instrument visible or displayed as the second virtual image 164B. However, the remaining objects do not match, therefore the graphical cues 165 still indicate the need to change position. The surgical instrument is close to the correct position and the system may provide information on how close the surgical instrument is to the planned position.

Figure 3E:
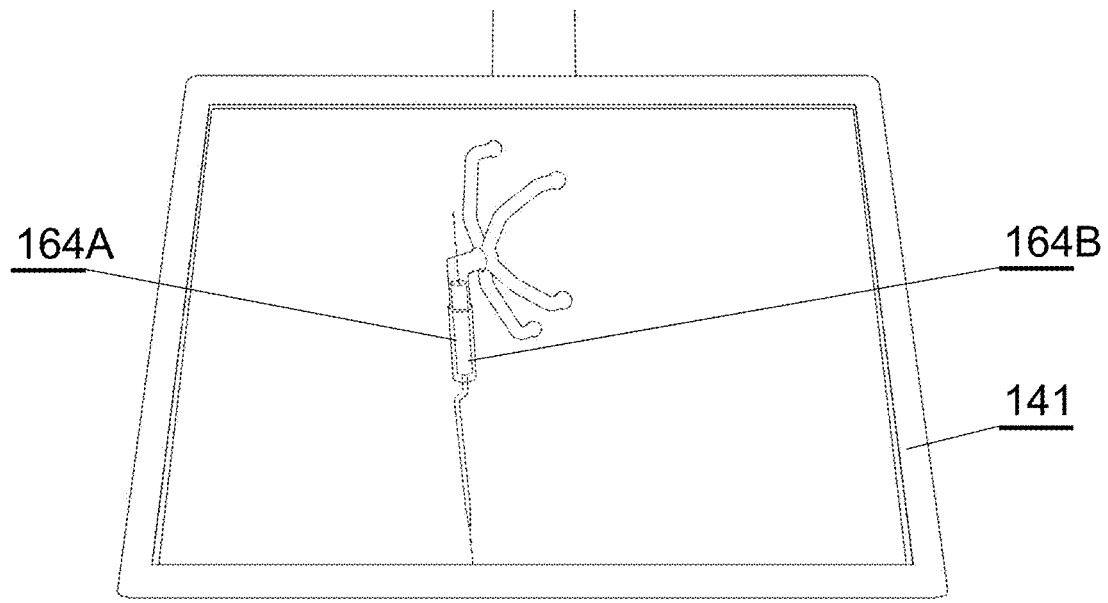
FIG. 3E shows an example of an augmented reality display in accordance with an embodiment of the invention.
Figure 3F:
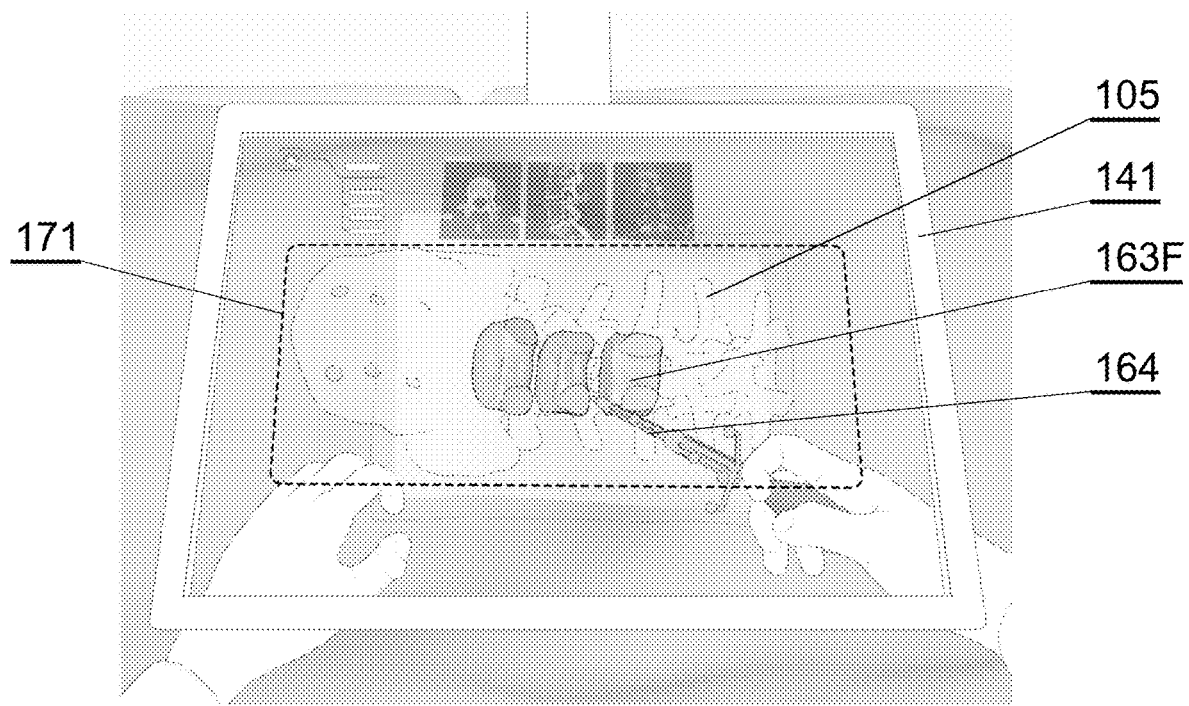
FIG. 3F shows an example of an augmented reality display in accordance with an embodiment of the invention.

FIG. 3E shows a situation wherein the supposed position of the real surgical instrument matches the position of the instrument according to the pre-operative plan 161, i.e. the correct position for surgery. In this situation the graphical cues 165 are no longer displayed, but the virtual images 164A, 164B may be changed to indicate the correct position, e.g. by highlighting it or blinking.

In some situations, the image of the full patient anatomy 163, as shown in FIG. 3A, may be obstructive. To solve this problem, the system allows a selective display of the parts of the anatomy 163, such that at least one part of the anatomy is shown and at least one other part of the anatomy is not shown.

For example, the surgeon may only want to see isolated parts of the spinal anatomy during spine surgery (only vertebral body or only the pedicle). Each part of the spinal anatomy is displayed at the request of the surgeon. For example the surgeon may only want to see the virtual representation of the pedicle during placement of bony anchors. This would be advantageous, as it would not have any visual interference from the surrounding anatomical structures.

Figure 3G:
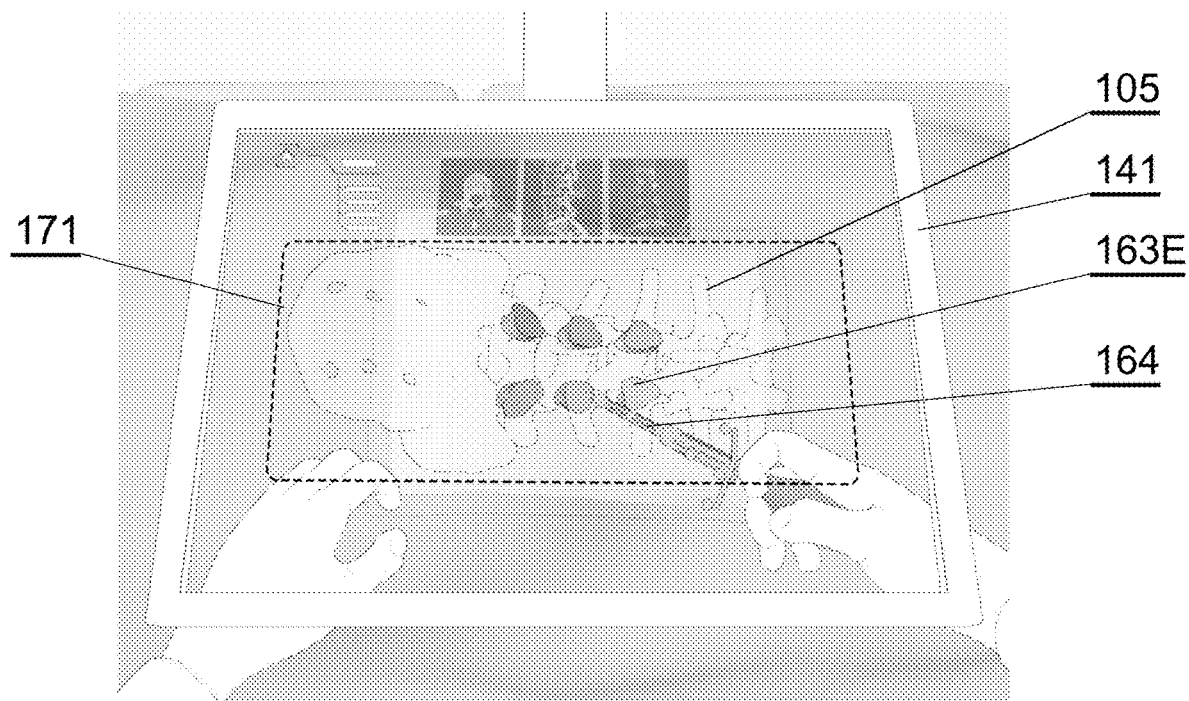
FIG. 3G shows an example of an augmented reality display in accordance with an embodiment of the invention.

Therefore, a single part of the anatomy may be displayed, for example only the vertebral body 163F (FIG. 3F) or only the pedicles 163E (FIG. 3G). Alternatively, two parts of the anatomy may be displayed, for example the vertebral body 163F and the pedicles 163E (FIG. 3H); or a larger group of anatomy parts may be displayed, such as the top parts of 163A-D of the spine (FIG. 3I).

The user may select the parts that are to be displayed via the input interface 132.

Figure 3H:
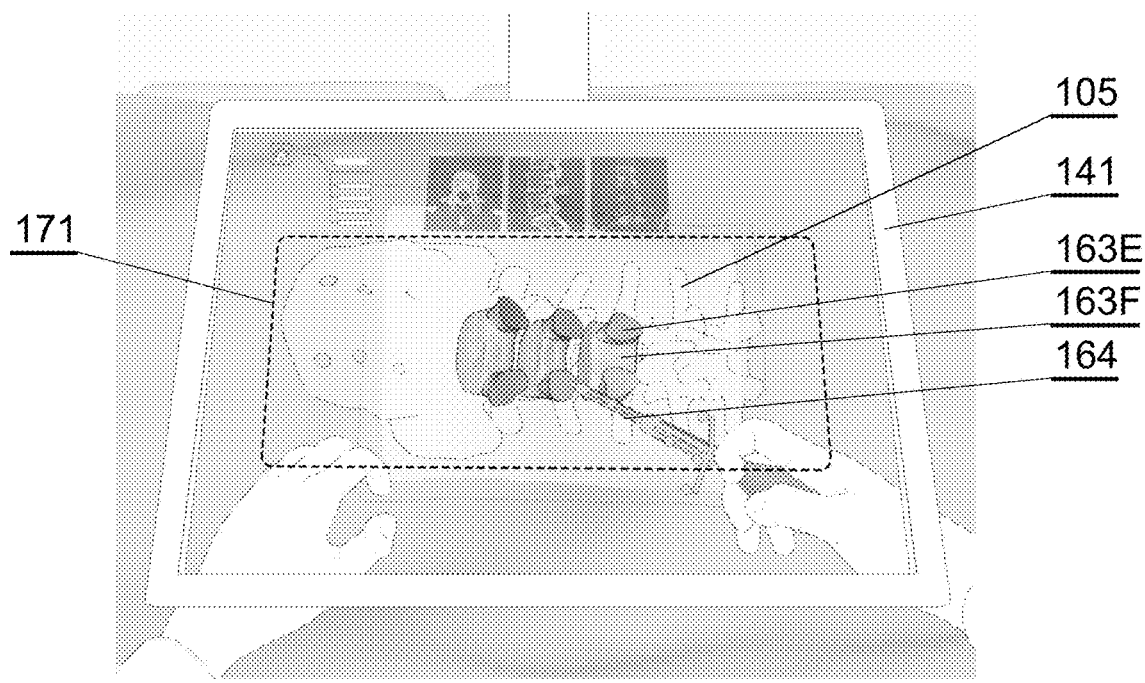
FIG. 3H shows an example of an augmented reality display in accordance with an embodiment of the invention.
Figure 3I:
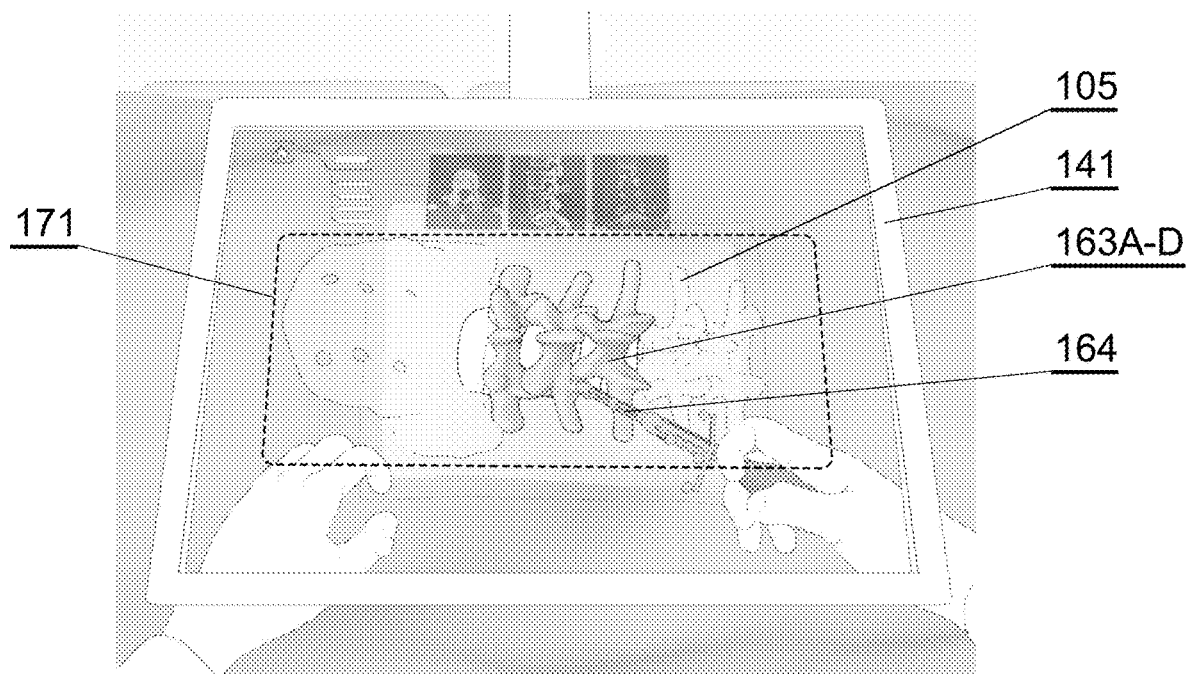
FIG. 3I shows an example of an augmented reality display in accordance with an embodiment of the invention.

For example, the GUI may comprise a set of predefined display templates, each template defining a particular part of the anatomy to be displayed (such as FIG. 3F, 3G) or a plurality of parts of the anatomy to be displayed (such as FIG. 3H, 3I). The user may then use a dedicated touch-screen button, keyboard key, pedal or other user interface navigation element to select a particular template to be displayed or to switch between consecutive templates.

Alternatively, the GUI may display a list of available parts of anatomy to be displayed and the user may select the parts to be displayed.

The GUI interface for configuring the parts that are to be displayed can be configured to be operated directly by the surgeon or by an assistant person.

The foregoing description will provide examples of a 3D display 142 with a see-through mirror 141, which is particularly effective to provide the surgical navigation data. However, other 3D display systems can be used as well to show the automatically segmented parts of anatomy, such as 3D head-mounted displays.

The see-through mirror (also called a half-silvered mirror) 141 is at least partially transparent and partially reflective, such that the viewer can see the real world behind the mirror but the mirror also reflects the surgical navigation image generated by the display apparatus located above it.

For example, a see-through mirror as commonly used in teleprompters can be used. For example, the see-through mirror 141 can have a reflective and transparent rate of 50R/50T, but other rates can be used as well.

The surgical navigation image is emitted from above the see-through mirror 141 by the 3D display 142.

Figure 4A:
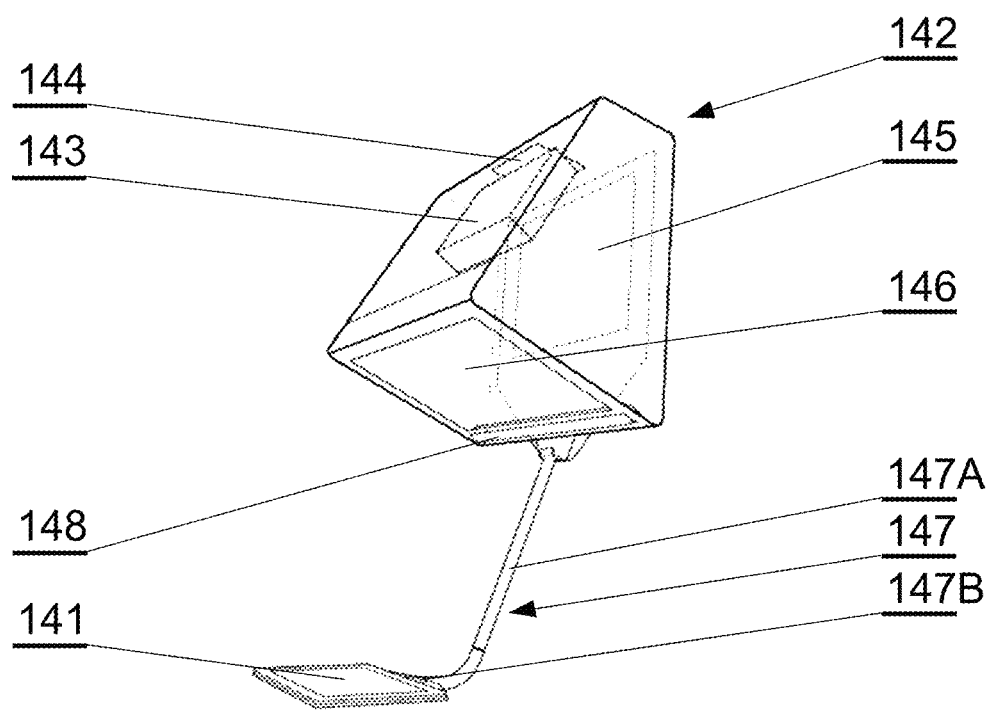
FIG. 4A shows a different embodiment of a 3D display system.
Figure 4C:
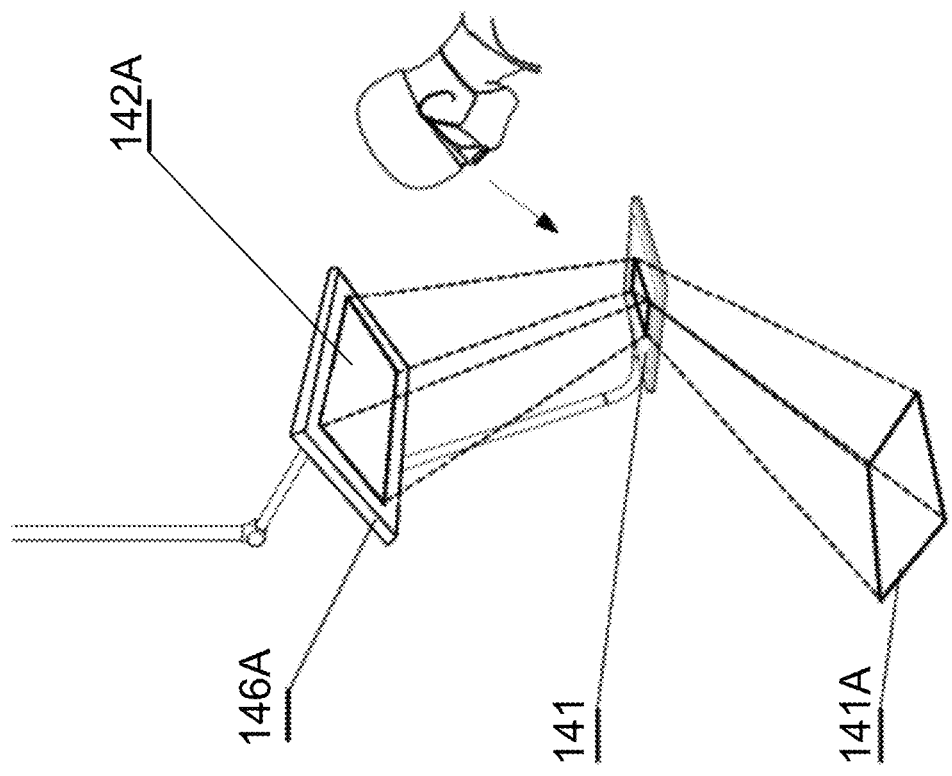
FIG. 4C shows another embodiment of a 3D display system.
Figure 4B:
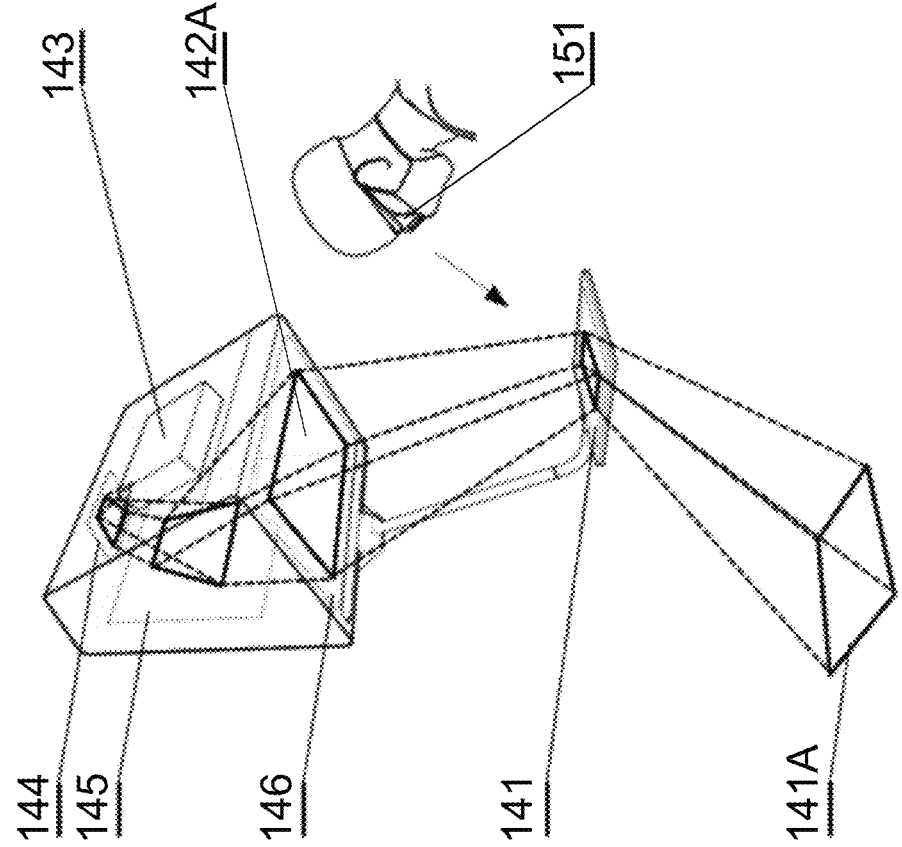
FIG. 4B shows another embodiment of a 3D display system.

In an example embodiment as shown in FIGS. 4A and 4B, a special design of the 3D display 142 is provided that is compact in size to facilitate its mounting within a limited space at the operating room. That design allows generating images of relatively large size, taking into account the small distance between the 3D display 142 and the see-through mirror 141, without the need to use wide-angle lens that could distort the image.

The 3D display 142 comprises a 3D projector 143, such as a DLP projector, that is configured to generate an image, as shown in FIG. 4B (by the dashed lines showing image projection and solid lines showing images generated on particular reflective planes). The image from the 3D projector 143 is firstly refracted by an opaque top mirror 144, then it is refracted by an opaque vertical mirror 145 and subsequently placed on the correct dimensions on a projection screen 146 (which can be simply a glass panel). The projection screen 146 works as a rear-projection screen or a small bright 3D display. The image displayed at the projection screen 146 is reflected by the see-through mirror 141 which works as an augmented reality visor. Such configuration of the mirrors 144, 145 allows the image generated by the 3D projector 143 to be shown with an appropriate size at the projection screen 146. The fact that the projection screen 146 emits an enlarged image generated by the 3D projector 143 makes the emitted surgical navigation image bright, and therefore well visible when reflected at the see-through mirror 141. Reference 141A indicates the augmented reality image as perceived by the surgeon when looking at the see-through mirror 141.

The see-through mirror 141 is held at a predefined position with respect to the 3D projector 143, in particular with respect to the 3D projector 143, by an arm 147, which may have a first portion 147A fixed to the casing of the 3D display 142 and a second portion 147B detachably fixed to the first portion 147A. The first portion 147A may have a protective sleeve overlaid on it. The second portion 147B, together with the see-through mirror 141, may be disposable in order to keep sterility of the operating room, as it is relatively close to the operating field and may be contaminated during the operation. The arm can also be foldable upwards to leave free space of the work space when the arm and augmented reality are not needed.

Figure 4E:
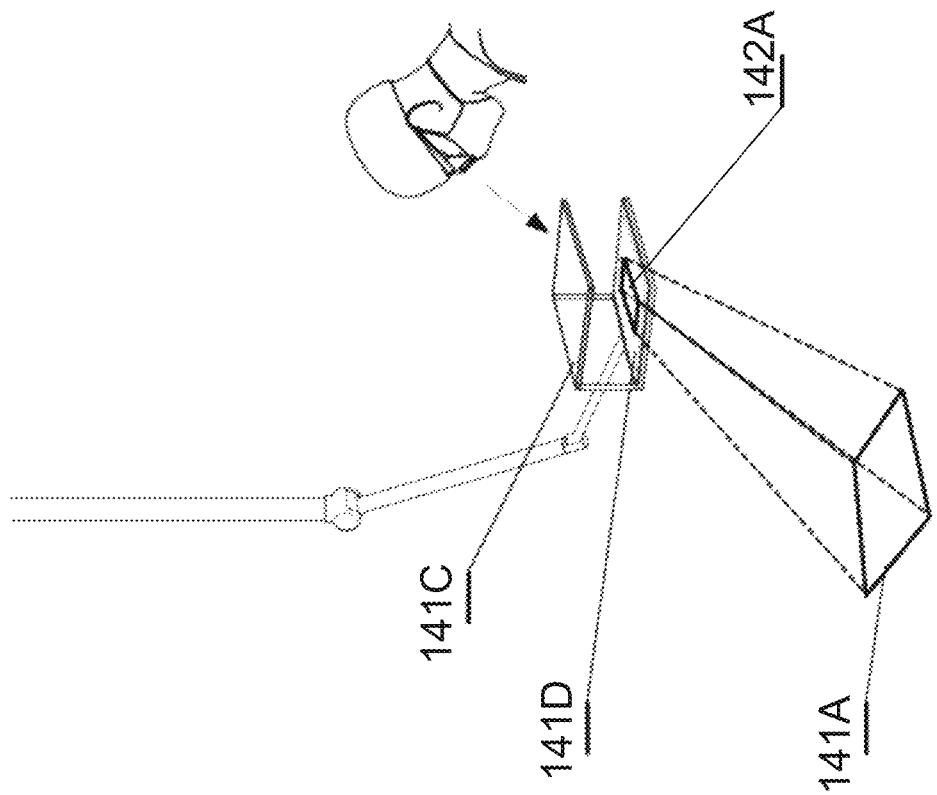
FIG. 4E shows another embodiment of a 3D display system.
Figure 4D:
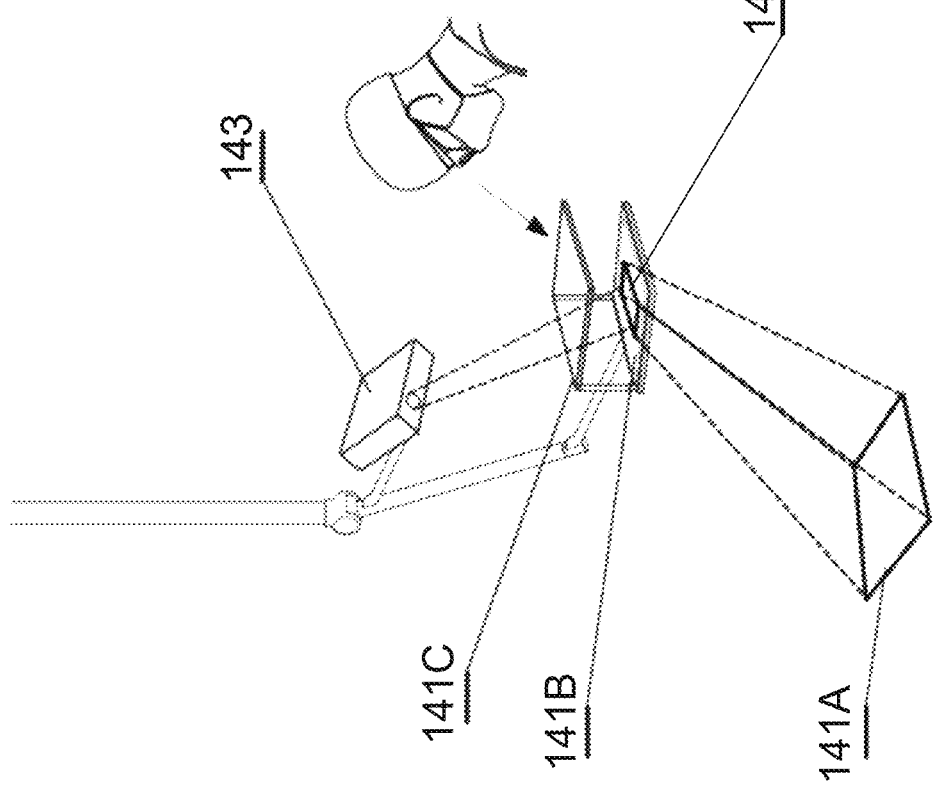
FIG. 4D shows another embodiment of a 3D display system.

In alternative embodiments, as shown for example in FIGS. 4C, 4D, 4E, alternative devices may be used in the 3D display system 140 in place of the see-through mirror 141 and the 3D display 142.

As shown in FIG. 4C, a 3D monitor 146A can be used directly in place of the projection screen 146.

As shown in FIG. 4D, a 3D projector 143 can be used instead of the 3D display 142 of FIG. 4A, to project the surgical navigation image onto a see-through projection screen 141B, which is partially transparent and partially reflective, for showing the surgical navigation image 142A and allowing the surgeon to see the surgical field 108. A lens 141C can be used to provide appropriate focal position of the surgical navigation image.

As shown in FIG. 4E, the surgical navigation image can be displayed at a three-dimensional see-through screen 141D and viewed by the user via a lens 141C used to provide appropriate focal position of the surgical navigation image.

Therefore, see-through screen 141B, the see-through display 141D and the see-through mirror 141 can be commonly called a see-through visor.

If a need arises to adapt the position of the augmented reality screen with respect to the surgeon's head (for example, to accommodate the position depending on the height of the particular surgeon), the position of the whole 3D display system 140 can be changed, for example by manipulating an adjustable holder (a surgical boom) 149 on FIG. 1A, by which the 3D display 142 is attachable to an operating room structure, such as a ceiling, a wall or a floor.

An eye tracker 148 module can be installed at the casing of the 3D display 142 or at the see-through visor 141 or at the wearable glasses 151, to track the position and orientation of the eyes of the surgeon and input that as commands via the gaze input interface to control the display parameters at the surgical navigation image generator 131, for example to activate different functions based on the location that is being looked at, as shown in FIGS. 5A and 5B.

For example, the eye tracker 148 may use infrared light to illuminate the eyes of the user without affecting the visibility of the user, wherein the reflection and refraction of the patterns on the eyes are utilized to determine the gaze vector (i.e. the direction at which the eye is pointing out). The gaze vector along with the position and orientation of the user's head is used to interact with the graphical user interface. However, other eye tracking algorithms techniques can be used as well.

It is particularly useful to use the eye tracker 148 along with the pedals 132 as the input interface, wherein the surgeon may navigate the system by moving a cursor by eyesight and inputting commands (such as select or cancel) by pedals.

FIGS. 7-14 show an example of a convolutional neural network (CNN) that can be used to automatically segment the bone structure to provide anatomy section data for the selective display as described above.

The CNN can be used to process images of a bony structure, such as a spine, skull, pelvis, long bones, shoulder joint, hip joint, knee joint etc. The foregoing description will present examples related mostly to a spine, but a skilled person will realize how to adapt the embodiments to be applicable to the other bony structures as well.

Moreover, the CNN may include, before segmentation, pre-processing of lower quality images to improve their quality. For example, the lower quality images may be low dose computed tomography (LDCT) images or magnetic resonance images captured with a relatively low power scanner can be denoised. The foregoing description will present examples related to computed tomography (CT) images, but a skilled person will realize how to adapt the embodiments to be applicable to other image types, such as magnetic resonance images.

FIGS. 7A-7E show examples of various CT images of a spine. FIGS. 7F-7J show their corresponding segmented images obtained by the method presented herein.

FIGS. 8A and 8B show an enlarged view of a CT scan, wherein FIG. 8A is an image with a high noise level (such as a low dose (LDCT) image) and FIG. 8B is an image with a low noise level (such as a high dose (HDCT) image or a LDCT image denoised according to the method presented herein).

FIG. 8C shows a low strength magnetic resonance scan of a neck portion and FIG. 8D shows a higher strength magnetic resonance scan of the same neck portion (wherein FIG. 8D is also the type of image that is expected to be obtained by performing denoising of the image of FIG. 8C).

Therefore, in the present CNN, a low-dose medical imagery (such as shown in FIG. 8A, 8C) is pre-processed to improve its quality to the quality level of a high-dose or high quality medical imagery (such as shown in FIG. 8B, 8D), without the need to expose the patient to the high dose imagery.

For the purposes of this disclosure, the LDCT image is understood as an image which is taken with an effective dose of X-ray radiation lower than the effective dose for the HDCT image, such that the lower dose of X-ray radiation causes appearance of higher amount of noise on the LDCT image than the HDCT image. LDCT images are commonly captured during intra-operative scans to limit the exposure of the patient to X-ray radiation.

As seen by comparing FIGS. 8A and 8B, the LDCT image is quite noisy and is difficult to be automatically processed by a computer to identify the components of the anatomical structure.

The system and method disclosed below use a neural network and deep-learning based approach. In order for any neural network to work, it must first be learned. The learning process is supervised (i.e., the network is provided with a set of input samples and a set of corresponding desired output samples). The network learns the relations that enable it to extract the output sample from the input sample. Given enough training examples, the expected results can be obtained.

In the presented system and method, a set of samples are generated first, wherein LDCT images and HDCT images of the same object (such as an artificial phantom or a lumbar spine) are captured using the computed tomography device. Next, the LDCT images are used as input and their corresponding HDCT images are used as desired output to learn the neutral network to denoise the images. Since the CT scanner noise is not totally random (there are some components that are characteristic for certain devices or types of scanners), the network learns which noise component is added to the LDCT images, recognizes it as noise and it is able to eliminate it in the following operation, when a new LDCT image is provided as an input to the network.

By denoising the LDCT images, the presented system and method may be used for intra-operative tasks, to provide high segmentation quality for images obtained from intra-operative scanners on low radiation dose setting.

Figure 10:
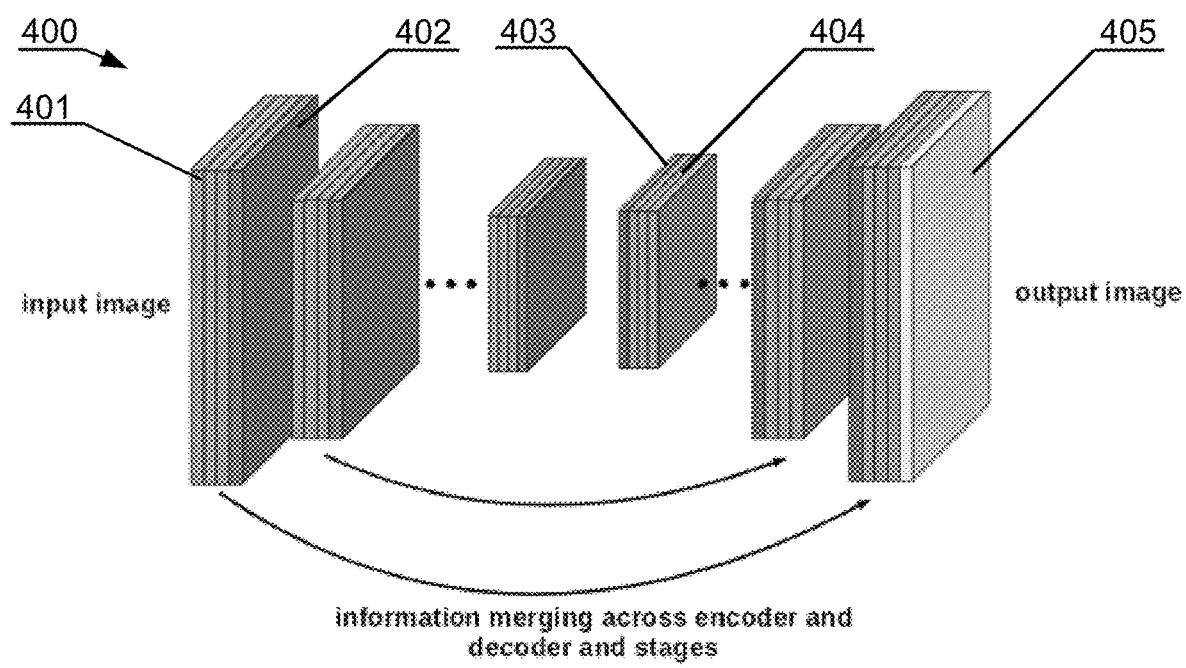
FIG. 10 shows a segmentation CNN architecture in accordance with an embodiment of the invention.

FIG. 10 shows a convolutional neural network (CNN) architecture 300, hereinafter called the denoising CNN, which is utilized in the present method for denoising. The network comprises convolution layers 301 (with ReLU activation attached) and deconvolution layers 302 (with ReLU activation attached). The use of a neural network in place of standard de-noising techniques provides improved noise removal capabilities. Moreover, since machine learning is involved, the network can be tuned to specific noise characteristics of the imaging device to further improve the performance. This is done during training. The architecture is general, in the sense that adopting it to images of different size is possible by adjusting the size (resolution) of the layers. The number of layers and the number of filters within layers is also subject to change, depending on the requirements of the application. Deeper networks with more filters typically give results of better quality. However, there's a point at which increasing the number of layers/filters does not result in significant improvement, but significantly increases the computation time, making such a large network impractical.

Figure 11:
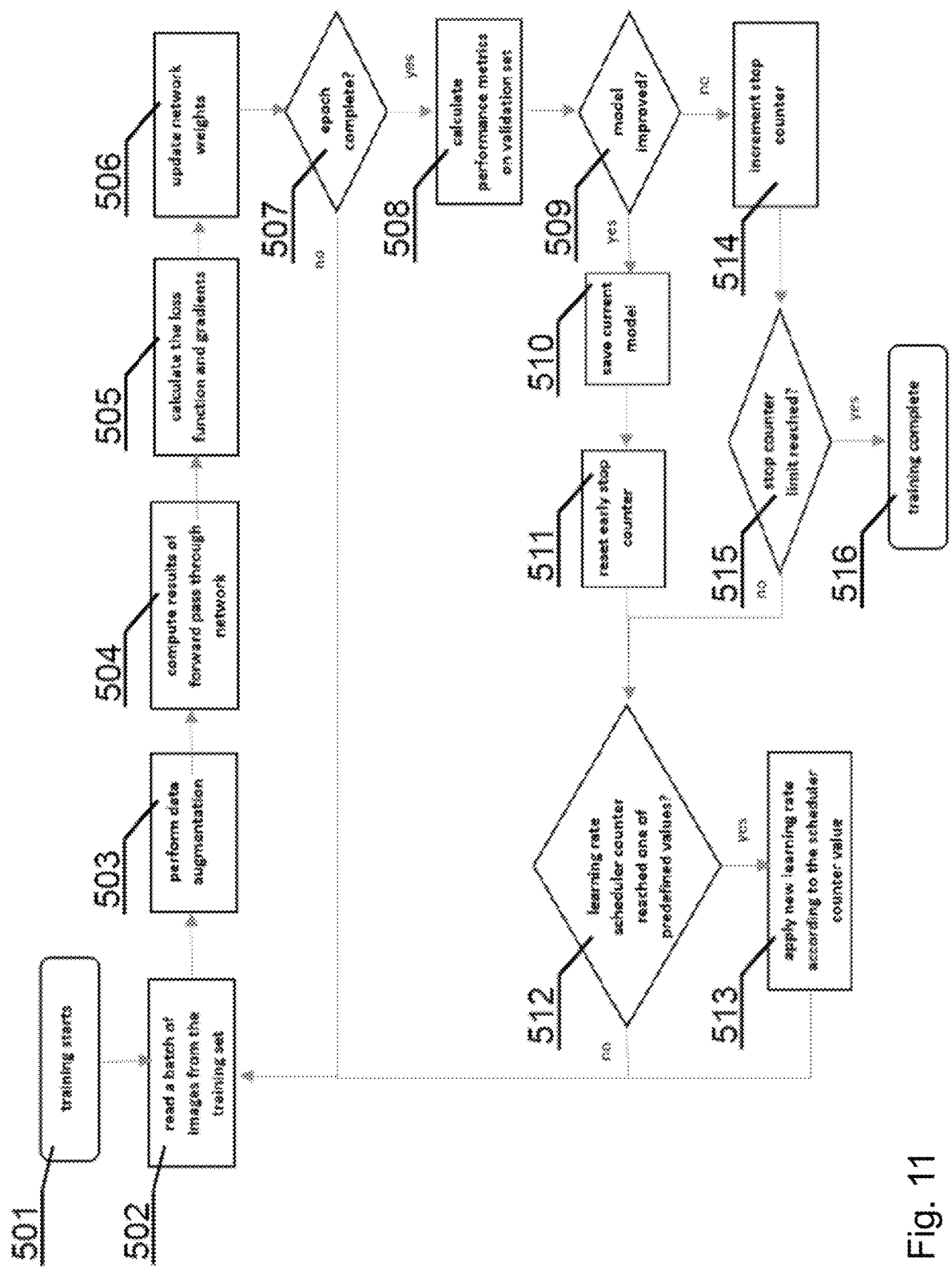
FIG. 11 shows a flowchart of a training process in accordance with an embodiment of the invention.

FIG. 11 shows a convolutional neural network (CNN) architecture 400, hereinafter called the segmentation CNN, which is utilized in the present method for segmentation (both semantic and binary). The network performs pixel-wise class assignment using an encoder-decoder architecture, using as input the raw images or the images denoised with the denoising CNN. The left side of the network is a contracting path, which includes convolution layers 401 and pooling layers 402, and the right side is an expanding path, which includes upsampling or transpose convolution layers 403 and convolutional layers 404 and the output layer 405.

One or more images can be presented to the input layer of the network to learn reasoning from single slice image, or from a series of images fused to form a local volume representation.

The convolution layers 401 can be of a standard kind, the dilated kind, or a combination thereof, with ReLU or leaky ReLU activation attached.

The upsampling or deconvolution layers 403 can be of a standard kind, the dilated kind, or a combination thereof, with ReLU or leaky ReLU activation attached.

The output slice 405 denotes the densely connected layer with one or more hidden layer and a softmax or sigmoid stage connected as the output.

The encoding-decoding flow is supplemented with additional skipping connections of layers with corresponding sizes (resolutions), which improves performance through information merging. It enables either the use of max-pooling indices from the corresponding encoder stage to downsample, or learning the deconvolution filters to upsample.

The architecture is general, in the sense that adopting it to images of different size is possible by adjusting the size (resolution) of the layers. The number of layers and number of filters within a layer is also subject to change, depending on the requirements of the application.

Deeper networks typically give results of better quality. However, there is a point at which increasing the number of layers/filters does not result in significant improvement, but significantly increases the computation time and decreases the network's capability to generalize, making such a large network impractical.

The final layer for binary segmentation recognizes two classes (bone and no-bone). The semantic segmentation is capable of recognizing multiple classes, each representing a part of the anatomy. For example, for the vertebra, this includes vertebral body, pedicles, processes etc.

FIG. 11 shows a flowchart of a training process, which can be used to train both the denoising CNN 300 and the segmentation CNN 400.

The objective of the training for the denoising CNN 300 is to tune the parameters of the denoising CNN 300 such that the network is able to reduce noise in a high noise image, such as shown in FIG. 8A, to obtain a reduced noise image, such as shown in FIG. 8B.

The objective of the training for the segmentation CNN 400 is to tune the parameters of the segmentation CNN 400 such that the network is able to recognize segments in a denoised image (such as shown in FIGS. 7A-7E or FIG. 8A) to obtain a segmented image (such as shown in FIGS. 7F-7J or FIG. 8B), wherein a plurality of such segmented images can be then combined to a 3D segmented image such as shown in FIG. 6.

The training database may be split into a training set used to train the model, a validation set used to quantify the quality of the model, and a test set.

The training starts at 501. At 502, batches of training images are read from the training set, one batch at a time. For the denoising CNN, LDCT images represent input, and HDCT images represent desired output. For the segmentation CNN, denoised images represent input, and pre-segmented (by a human) images represent output.

At 503 the images can be augmented. Data augmentation is performed on these images to make the training set more diverse. The input/output image pair is subjected to the same combination of transformations from the following set: rotation, scaling, movement, horizontal flip, additive noise of Gaussian and/or Poisson distribution and Gaussian blur, etc.

At 504, the images and generated augmented images are then passed through the layers of the CNN in a standard forward pass. The forward pass returns the results, which are then used to calculate at 505 the value of the loss function—the difference between the desired output and the actual, computed output. The difference can be expressed using a similarity metric, e.g.: mean squared error, mean average error, categorical cross-entropy or another metric.

At 506, weights are updated as per the specified optimizer and optimizer learning rate. The loss may be calculated using a per-pixel cross-entropy loss function and the Adam update rule.

The loss is also back-propagated through the network, and the gradients are computed. Based on the gradient values, the network's weights are updated. The process (beginning with the image batch read) is repeated continuously until an end of the training session is reached at 507.

Then, at 508, the performance metrics are calculated using a validation dataset—which is not explicitly used in training set. This is done in order to check at 509 whether not the model has improved. If it isn't the case, the early stop counter is incremented at 514 and it is checked at 515 if its value has reached a predefined number of epochs. If so, then the training process is complete at 516, since the model hasn't improved for many sessions now.

If the model has improved, the model is saved at 510 for further use and the early stop counter is reset at 511. As the final step in a session, learning rate scheduling can be applied. The session at which the rate is to be changed are predefined. Once one of the session numbers is reached at 512, the learning rate is set to one associated with this specific session number at 513.

Once the training is complete, the network can be used for inference, i.e. utilizing a trained model for prediction on new data.

Figure 12:
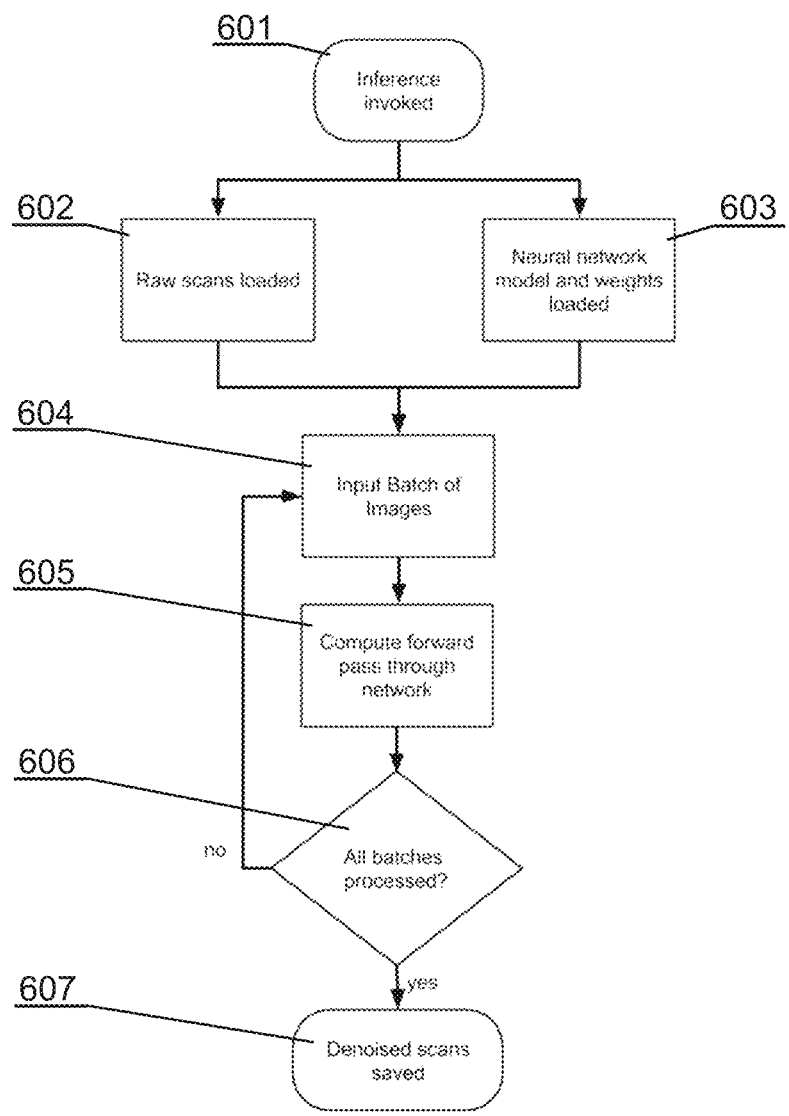
FIG. 12 shows a flowchart of an inference process for the denoising CNN in accordance with an embodiment of the invention.

FIG. 12 shows a flowchart of an inference process for the denoising CNN 300.

After inference is invoked at 601, a set of scans (LDCT, not denoised) are loaded at 602 and the denoising CNN 300 and its weights are loaded at 603.

At 604, one batch of images at a time is processed by the inference server. At 605, a forward pass through the denoising CNN 300 is computed.

At 606, if not all batches have been processed, a new batch is added to the processing pipeline until inference has been performed at all input noisy LDCT images.

Finally, at 607, the denoised scans are saved.

Figure 13:
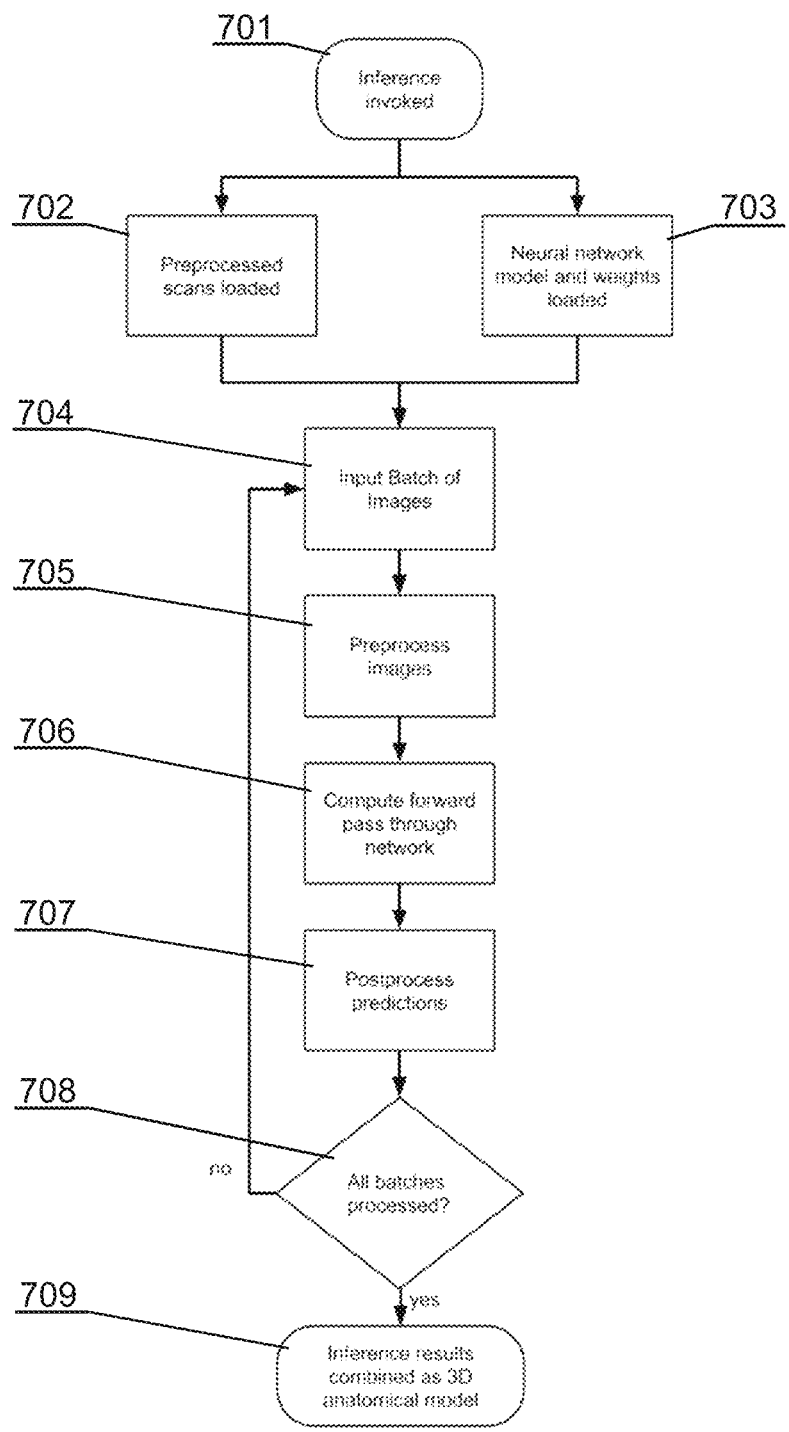
FIG. 13 shows a flowchart of an inference process for the segmentation CNN in accordance with an embodiment of the invention.

FIG. 13 shows a flowchart of an inference process for the segmentation CNN 400.

After inference is invoked at 701, a set of scans (denoised images obtained from noisy LDCT images) are loaded at 702 and the segmentation CNN 400 and its weights are loaded at 703.

At 704, one batch of images at a time is processed by the inference server.

At 705, the images are preprocessed (e.g., normalized, cropped) using the same parameters that were utilized during training, as discussed above. In at least some implementations, inference-time distortions are applied and the average inference result is taken on, for example, 10 distorted copies of each input image. This feature creates inference results that are robust to small variations in brightness, contrast, orientation, etc.

At 706, a forward pass through the segmentation CNN 400 is computed.

At 707, the system may perform post-processing such as linear filtering (e.g. Gaussian filtering), or nonlinear filtering, such as median filtering and morphological opening or closing.

At 708, if not all batches have been processed, a new batch is added to the processing pipeline until inference has been performed at all input images.

Finally, at 709, the inference results are saved and can be combined to a segmented 3D model. The model can be further converted to a polygonal mesh representation for the purpose of visualization on the display. The volume and/or mesh representation parameters can be adjusted in terms of change of color, opacity, changing the mesh decimation depending on the needs of the operator.

Figures 14A, 14B:
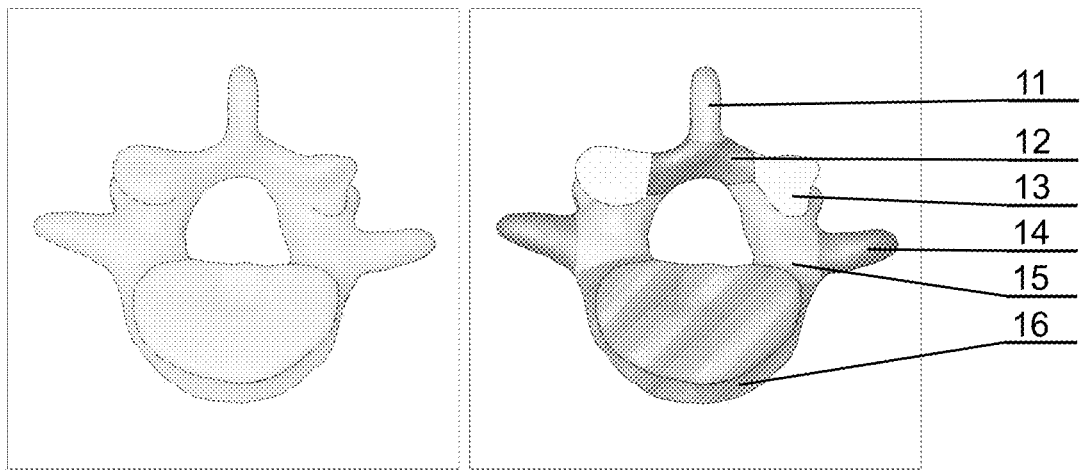
FIG. 14A shows a sample image of a CT spine scan.
FIG. 14B shows a sample image of the segmentation of the sample image of FIG. 14A in accordance with an embodiment of the invention.

FIG. 14A shows a sample image of a CT spine scan and FIG. 14B shows a sample image of its segmentation. Every class (anatomical part of the vertebrae) can be denoted with its specific color. The segmented image comprises spinous process 11, lamina 12, articular process 13, transverse process 14, pedicles 15, vertebral body 16.

FIG. 6 shows a sample of the segmented images displaying all the parts of the vertebrae (11-16) obtained after the semantic segmentation combined into a 3D model.

The functionality described herein can be implemented in a computer system. The system may include at least one non-transitory processor-readable storage medium that stores at least one of processor-executable instructions or data and at least one processor communicably coupled to that at least one non-transitory processor-readable storage medium. That at least one processor is configured to perform the steps of the methods presented herein.

Figure 15:
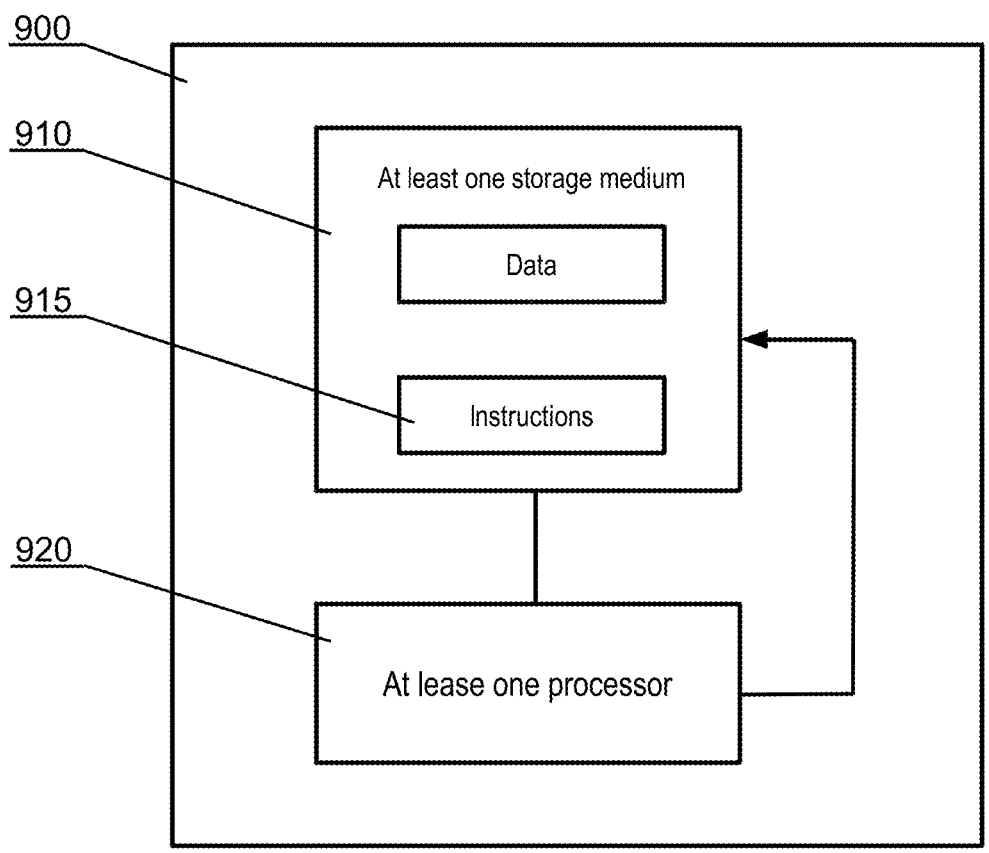
FIG. 15 shows a schematic of a system for implementing the segmentation CNN in accordance with an embodiment of the invention.

FIG. 15 shows a schematic illustration of a computer-implemented system 900, for example a machine learning system, in accordance with one embodiment of the invention, for implementing the segmentation CNN. The system 900 may include at least one non-transitory processor-readable storage medium 910 that stores at least one of processor-executable instructions 915 or data; and at least one processor 920 communicably coupled to the at least one non-transitory processor-readable storage medium 910. The at least one processor 920 may be configured to (by executing the instructions 915) receive segmentation learning data comprising a plurality of batches of labeled anatomical image sets, each image set comprising image data representative of a series of slices of a three-dimensional bony structure, and each image set including at least one label which identifies the region of a particular part of the bony structure depicted in each image of the image set, wherein the label indicates one of a plurality of classes indicating parts of the bone anatomy. The at least one processor 920 may also be configured to (by executing the instructions 915) train a segmentation CNN, that is a fully convolutional neural network model with layer skip connections, to segment into plurality of classes at least one part of the bony structure utilizing the received segmentation learning data. The at least one processor 920 may also be configured to (by executing the instructions 915) store the trained segmentation CNN in at least one non-transitory processor-readable storage medium 910 of the machine learning system.

While the invention has been described with respect to a limited number of embodiments, it will be appreciated that many variations, modifications and other applications of the invention may be made. Therefore, the claimed invention as recited in the claims that follow is not limited to the embodiments described herein.

What is claimed is:

1. A surgical navigation system, comprising:
a source of a patient anatomy data, the patient anatomy data including image data of patient spinal anatomy and segmentation data of the patient spinal anatomy that provides a three-dimensional (3D) reconstruction of a segmented model of the patient spinal anatomy including a set of sections each representing different parts of the patient spinal anatomy;
a processor configured to generate a set of surgical navigation images including different subsets of sections of the set of sections using the patient anatomy data; and
a 3D display system including a non-head mounted 3D display and a see-through mirror, the 3D display configured to selectively project images from the set of surgical navigation images onto the see-through mirror such that the see-through mirror displays at least:
a first surgical navigation image of the set of surgical navigation images in which a first section of the set of sections is displayed together with a second section of the set of sections; and
a second surgical navigation image of the set of surgical navigation images in which the second section is displayed with the first section being hidden such that the first section does not interfere with the display of the second section.

2. The system of claim 1, further comprising:
a tracking system configured to track a head of a surgeon operating on the patient spinal anatomy, one or more components of the 3D display system, and a physical location of the patient spinal anatomy to provide position or orientation data to the processor,
the processor configured to generate the set of surgical navigation images based on the position or orientation data provided by the tracking system.

3. The system of claim 2, further comprising:
a source of at least one of operative plan data of an operative plan and a virtual surgical instrument model of a surgical instrument,
wherein the tracking system is further configured to track the surgical instrument;
wherein at least one surgical navigation image from the set of surgical navigation images further includes a virtual image of the surgical instrument.

4. The system of claim 3, wherein the virtual image of the surgical instrument is configured to indicate a suggested position or orientation of the surgical instrument according to the operative plan data.

5. The system of claim 4, wherein the at least one surgical navigation image further includes a graphical cue indicating a required change of a position or orientation of the surgical instrument to match the suggested position or orientation according to the operative plan data.

6. The system of claim 1, wherein the set of surgical navigation images further includes a set of orthogonal or arbitrary planes of the patient spinal anatomy.

7. The system of claim 1, wherein the see-through mirror is positioned between a head of a surgeon operating on the patient spinal anatomy and a surgical field including the patient spinal anatomy such that the set of surgical navigation images are collocated with the patient spinal anatomy in the surgical field to form an augmented reality image that is visible to the surgeon looking from above the see-through mirror towards the surgical field.

8. The system of claim 1, wherein the patient anatomy data includes output data of a semantic segmentation process of a set of two-dimensional (2D) images of the patient spinal anatomy.

9. The system of claim 8, further comprising a convolutional neural network (CNN) system configured to perform the semantic segmentation process to generate the patient anatomy data.

10. The system of claim 9, wherein the processor is a first processor, and the CNN system includes:
at least one non-transitory processor-readable storage medium that stores at least one of processor-executable instructions or data; and
at least one second processor communicably coupled to the at least one non-transitory processor-readable storage medium, wherein that at least one second processor is configured to:
receive segmentation learning data comprising a plurality of labeled anatomical image sets, each labeled anatomical image set from the plurality of labeled anatomical image sets including: (1) image data including a series of 2D images of the patient spinal anatomy, and (2) at least one label that identifies at least one part of one or more vertebrae of the patient spinal anatomy depicted in each 2D image of the image set, wherein the at least one label identifies one class of a plurality of classes indicating different parts of the one or more vertebrae of the patient spinal anatomy;
train a segmentation CNN model to segment semantically the patient spinal anatomy utilizing the received segmentation learning data; and
store the trained segmentation CNN model in the at least one non-transitory processor-readable storage medium.

11. The system of claim 10, wherein the at least one second processor is further configured to:
receive denoising learning data comprising a plurality of high quality medical images and low quality medical images, wherein the high quality medical images have a lower noise level than the low quality medical images;
train a denoising CNN model to denoise an image utilizing the received denoising learning data; and
store the trained denoising CNN model in the at least one non-transitory processor-readable storage medium.

12. The system of claim 11, wherein the at least one second processor is further configured to operate the trained denoising CNN model to process the set of 2D images of the patient spinal anatomy to generate a set of output denoised images of the patient spinal anatomy.

13. The system of claim 12, wherein the set of 2D images of the patient spinal anatomy includes low quality medical images.

14. The system of claim 10, wherein the at least one second processor is further configured to operate the trained segmentation CNN model to process the set of 2D images of the patient spinal anatomy to generate a set of output segmented images of the patient spinal anatomy.

15. The system of claim 1, wherein the processor is configured to generate the set of surgical navigation images including the different subsets of sections by processing the patient anatomy data using a set of predefined templates, each predefined template of the set of predefined templates defining a different combination of one or more parts of the patient spinal anatomy.

16. The surgical navigation system of claim 1, wherein each of the set of sections represents a different part of one or more vertebrae of the spine including: a pedicle, a spinous process, a lamina, an articular process, a transverse process, or a vertebral body.

17. A method for providing an augmented reality image during an operation, comprising:
   obtaining a source of a patient anatomy data,
   the patient anatomy data including image data of patient spinal anatomy and segmentation data of the patient spinal anatomy that provides a three-dimensional (3D) reconstruction of a segmented model of the patient spinal anatomy including a set of sections each representing different parts of the patient spinal anatomy;
   generating, by a processor, a set of surgical navigation images including different subsets of sections of the set of sections using the patient anatomy data;
   receiving a selection of a subset of sections; and
   displaying, via a 3D display system including a non-head mounted 3D display and a see-through mirror, a surgical navigation image from the set of surgical navigation images including only the subset of sections of the selection while the remaining sections of the set of sections not in the selection are hidden such that the subset of sections is displayed without interference from the remaining sections of the set of sections.

18. The method of claim 17, wherein generating the set of surgical navigation images includes processing the patient anatomy data using a set of predefined templates, each predefined template of the set of predefined templates defining a different combination of one or more parts of the patient spinal anatomy.

19. The method of claim 17, further comprising:
   receiving a sequence of additional selections of subsets of sections;
   displaying, via the 3D display system, additional surgical navigation images from the set of surgical navigation images that include the subsets of sections of the additional selections according to the sequence.

20. The method of claim 17, wherein the surgical navigation image displayed via the 3D display system further includes a virtual image of a surgical instrument.

21. A method, comprising:
   receiving patient anatomy data, the patient anatomy data including image data of patient spinal anatomy and segmentation data of the patient spinal anatomy that provides a three-dimensional (3D) reconstruction of a segmented model of the patient spinal anatomy including a set of sections each representing different parts of the patient spinal anatomy;
   generating a graphical user interface including a set of display templates, each display template from the set of display templates defining a different combination of one or more parts of the patient spinal anatomy;
   in response to a user selection of a first display template from the set of display templates, displaying, using a 3D display system, a first surgical navigation image in which a first section of the set of sections is displayed together with a second section of the set of sections; and
   in response to a user selection of a second display template from the set of display templates, displaying, using the 3D display system, a second surgical navigation image of the set of surgical navigation images in which the second section is displayed with the first section being hidden such that the first section does not interfere with the display of the second section.

* * * * *